(12) United States Patent
Carlisle et al.

(10) Patent No.: US 7,654,982 B2
(45) Date of Patent: Feb. 2, 2010

(54) FLOW CONTROL SYSTEM AND METHOD WITH VARIABLE PRESSURE AND VARIABLE RESISTANCE

(75) Inventors: Jeffrey A. Carlisle, Stratham, NH (US); Lawrence M. Kuba, Nashua, NH (US); John M. Kirkman, Jr., Trumansburg, NY (US)

(73) Assignee: Fluidnet Corporation, Portsmouth, NH (US)

( * ) Notice: Subject to any disclaimer, the term of this patent is extended or adjusted under 35 U.S.C. 154(b) by 0 days.

(21) Appl. No.: 12/280,924

(22) PCT Filed: Feb. 27, 2007

(86) PCT No.: PCT/US2007/005095

§ 371 (c)(1),
(2), (4) Date: Aug. 27, 2008

(87) PCT Pub. No.: WO2007/098287

PCT Pub. Date: Aug. 30, 2007

(65) Prior Publication Data

US 2009/0026146 A1     Jan. 29, 2009

Related U.S. Application Data

(60) Provisional application No. 60/777,193, filed on Feb. 27, 2006.

(30) Foreign Application Priority Data

Jan. 23, 2007   (WO) .............. PCT/US2007/002039

(51) Int. Cl.
*A61B 17/50*   (2006.01)
(52) U.S. Cl. .................................. 604/132
(58) Field of Classification Search ............... 604/30, 604/31, 65, 66, 67, 890.1, 131–135, 140–143, 604/145–147, 150, 153–155, 214, 216–218, 604/225–228, 232; 222/92, 95, 103, 386
See application file for complete search history.

(56) References Cited

U.S. PATENT DOCUMENTS

| | | | |
|---|---|---|---|
| 4,090,514 A | 5/1978 | Hinck et al. | |
| 4,191,184 A | 3/1980 | Carlisle | |
| 4,470,758 A | 9/1984 | Pazemenas et al. | |

(Continued)

FOREIGN PATENT DOCUMENTS

WO   WO2007/098265 A2   8/2007

(Continued)

OTHER PUBLICATIONS

International Search Report and Written Opinion of the International Searching Authority dated Mar. 4, 2008, received in PCT/US2007/04945.

(Continued)

*Primary Examiner*—Manuel A Mendez
(74) *Attorney, Agent, or Firm*—McLane, Graf, Raulerson & Middleton, P.A.; Scott C. Rand

(57) ABSTRACT

An infusion pump and method are provided which control flow rates with variable fluid pressure and variable series flow resistance.

20 Claims, 17 Drawing Sheets

U.S. PATENT DOCUMENTS

| | | | |
|---|---|---|---|
| 4,539,005 A | | 9/1985 | Greenblatt |
| 4,561,298 A | | 12/1985 | Pond |
| 4,976,162 A | | 12/1990 | Kamen |
| 5,207,645 A | | 5/1993 | Ross et al. |
| 5,308,335 A | * | 5/1994 | Ross et al. ............... 604/141 |
| 5,348,539 A | | 9/1994 | Herskowitz |
| 5,433,704 A | | 7/1995 | Ross et al. |
| 5,464,391 A | | 11/1995 | DeVale |
| 5,533,381 A | | 7/1996 | Seale |
| 5,554,123 A | | 9/1996 | Herskowitz |
| 5,584,811 A | | 12/1996 | Ross et al. |
| 5,597,042 A | * | 1/1997 | Tubel et al. ............ 166/250.01 |
| 5,624,409 A | | 4/1997 | Seale |
| RE35,501 E | | 5/1997 | Ross et al. |
| 5,743,878 A | | 4/1998 | Ross et al. |
| 5,769,608 A | | 6/1998 | Seale |
| 5,788,674 A | | 8/1998 | McWilliams |
| 6,275,284 B1 | | 8/2001 | Kiel et al. |
| 6,398,760 B1 | | 6/2002 | Danby |
| 6,461,323 B2 | | 10/2002 | Fowler et al. |
| 6,641,562 B1 | | 11/2003 | Peterson |
| 6,642,999 B2 | | 11/2003 | Arndt et al. |
| 6,685,668 B1 | | 2/2004 | Cho et al. |
| 6,981,960 B2 | | 5/2004 | Cho et al. |
| 7,503,903 B2 | | 3/2009 | Carlisle et al. |
| 2005/0235733 A1 | | 10/2005 | Holst et al. |

FOREIGN PATENT DOCUMENTS

WO  WO2007/106232 A2  9/2007

OTHER PUBLICATIONS

International Search Report and Written Opinion of the International Searching Authority dated Mar. 4, 2008, received in PCT/US2007/05095.

* cited by examiner

FLOW CONTROL SYSTEM AND METHOD WITH VARIABLE PRESSURE AND VARIABLE RESISTANCE

BACKGROUND

The present disclosure relates to fluid flow control systems, such as intravenous infusion pumps, and more particularly to feedback control infusion pumps with flow sensing, volume sensing, variable pressure control, and variable flow resistance.

A conventional large volume infusion pump is typically equipped with a motor that, in connection with a mechanical assembly and through the interface of a fluid barrier, pushes a small amount of fluid per motor "step." The mechanism might be a cam, a leadscrew, or other such assembly. The fluid barrier might be a syringe, an extruded tube, a molded cassette, or other such device that separates the pumping mechanism from the fluid in question. In each case, the fluid movement is determined by a certain number of motor steps over time.

At slow flow rates, the motor steps are relatively infrequent with long dwell periods. At high flow rates, the motor and mechanism are run at their maximal capacity until one element has reached its engineering limit. The flow rate is inherently pulsatile, yet this pulsatile nature is less significant at higher flow rates where the natural compliance of the outlet of the pumps serves to dampen the pulses into more or less a continuous stream of fluid.

The motors used conventionally are inherently powerful enough to overcome significant forces and resistances, so they are capable of generating significant pumping forces. This forceful pumping is an artifact and has no desirable clinical effect. The sensing mechanisms commonly used are pressure based and made with indirect contact with the fluid to be pumped. In most cases, the fluid barrier, such as an extruded tube, exerts far more force than the internal fluid pressures. The result is a lack of sensitivity to pressure changes and a lack of feedback as to the actual conditions of fluid flow. It is common for conventional pumps to operate indefinitely without recognizing that the actual fluid flow rate is far below the targeted level.

Conventional motor driven pumps are notoriously inefficient with respect to external power consumption. For devices that have a high requirement for portability, this power inefficiency translates into unreliable operation.

Prior to the use of pumps, most infusions were done by the adjustment of a gravity-based pressure (e.g., by adjusting the height of a liquid container) and the adjustment of inline resistance (e.g., by moving the position of a roller clamp), both in response to an inline flow sensing method (e.g., performed by a user counting drops into an air chamber). Although this prior art method was labor intensive and had limited rate range, it offered some significant advantages over the subsequent "advances" in technology. First, the use of gravity head heights for a delivery pressure was energy efficient. No external power supply was required. Second, the pressure was low, so the dangers of high-pressure infusions were avoided. Third, the gravity infusions could be augmented with a low cost and readily available pressure cuff, supplementing the fluid flow to rates well above those possible by an instrumented "pump" line. Forth, a gravity administration was not capable of infusing large amounts of air into the output line, because the hydrostatic pressure goes to zero as the fluid source empties.

The present disclosure seeks to combine the meritorious aspects of a conventional "gravity" infusion with the benefits of a controlled intravenous infusion pump. In each aspect, this disclosure takes the desired principles of a gravity infusion and reduces the dependence upon skilled labor and extends the range and precision of fluid flow control and provides advanced information management capabilities.

An ideal embodiment of an infusion device would be one with continuous flow, wide flow rate range, high energy efficiency, accuracy of volume delivered over time, minimal operating pressures, maximum sensitivity to external conditions, freedom from false alarms for air-in-line, simplicity, low cost, intuitive operation, automated information exchange, safety, and reliability.

Certain infusions have historically been managed by air pressure delivery systems, most commonly found in the operating room and in emergency situations. Prior art attempts have been made to determine the flow rate via pressure monitoring and control. For example, U.S. Pat. No. 5,207,645 to Ross et al. discloses pressurizing an IV bag and monitoring pressure to infer flow rates. However, the prior art systems lack independent flow sensing, and, therefore, do not offer enough information to provide accurate and safe infusions.

Under the best of circumstances, there is not enough information in the pressure signal alone to provide the accuracy needed for intravenous infusion therapy. Furthermore, there are a number of likely failure modes that would go undetected using the pressure signal alone. An infusion pump must be able to respond to events in a relevant time frame. International standards suggest that a maximum period of 20 seconds can lapse before fluid delivery is considered "non-continuous." As an example, for an infusion of 10 ml/h, the system would want to resolve 20 seconds of flow, which corresponds to 0.056 mL. This volume represents one part in 180,000 of the total air volume. Temperature induced change in pressure brought about by a normal air conditioning cycle is far greater than this signal. The measurement of pressure alone is not adequate for an intravenous infusion device. No general purpose, full range, infusion devices using pressure-controlled delivery are known to be on the market.

An entire class of "passive" infusion pumps exists whereby a constant pressure is created on a fluid filled container by way of a spring, elastomeric structure, gas producing chemical equilibrium, or other means. This constant pressure fluid is fed into a high resistance output line, providing relatively stable fluid flow.

In typical pressure based flow control products, a relatively high pressure pushes fluid into a known, high, and fixed resistance, providing a constant flow rate with good immunity from changes in external conditions. It is the purpose of this disclosure to provide a highly flexible flow control system with a very broad flow rate range, operating under minimal pressures, with a relatively low and variable resistance.

It would therefore be useful to develop a device that could control fluid flow based on a responsive fluid flow sensing means that forms a closed loop control by changing both the fluid driving pressure and the inline resistance. In contrast to the conventional approach to flow control wherein a user observes fluid flowing as it formed drops in an air chamber, then adjusts pressure by varying the head height of the fluid source, and then adjusts the inline resistance via a manual valve, the present disclosure provides an apparatus and method that automatically and accurately measures fluid flow rate, precisely adjusts the hydrostatic pressure of the fluid source, and precisely adjusts inline fluid flow resistance to achieve or maintain a target flow rate.

SUMMARY

A fluid control system and method are disclosed which combine the measurement of flow rate, an adjustable fluid pressure, and an adjustable inline resistance.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
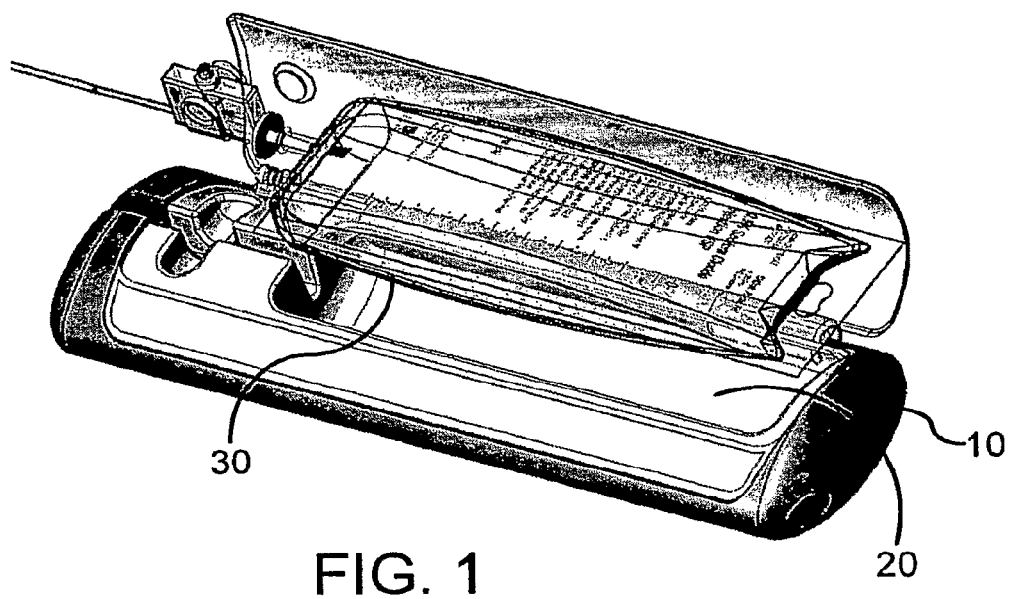
FIGS. 1 and 2 are perspective and side views, respectively, of an infusion pump in accordance with an exemplary embodiment.
Figure 2:
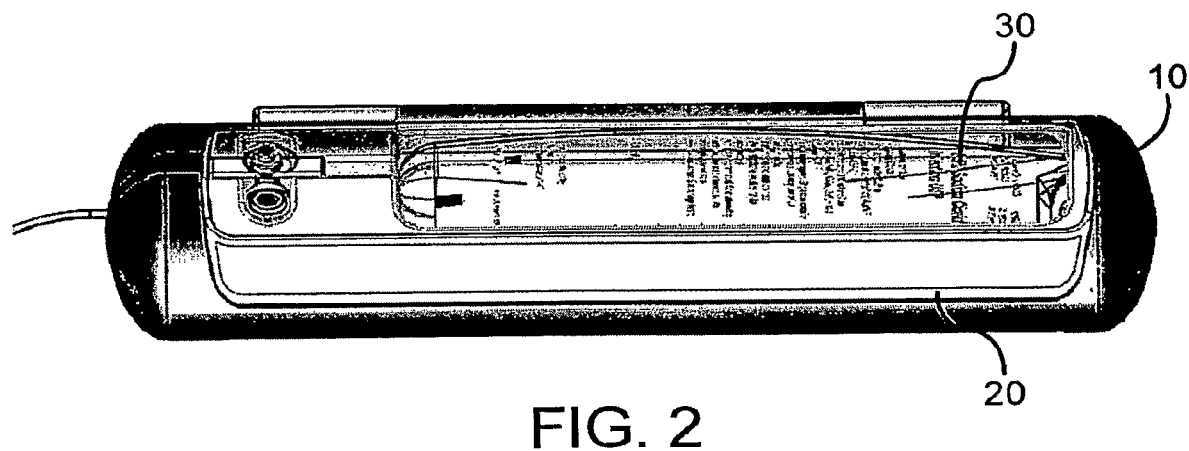

Referring to the drawings, wherein like numerals reference numerals are used to indicate like or analogous components throughout the several views, FIGS. 1 and 2 depict an exemplary volume and flow measurement system in accordance with an exemplary embodiment of the present invention. The system includes a pressure frame 10 that is of known total volume and contains within it an air bladder 20 and a flexible bag 30 that contains within it a liquid 40 (see FIGS. 3 and 4) to be infused.

Figure 3:
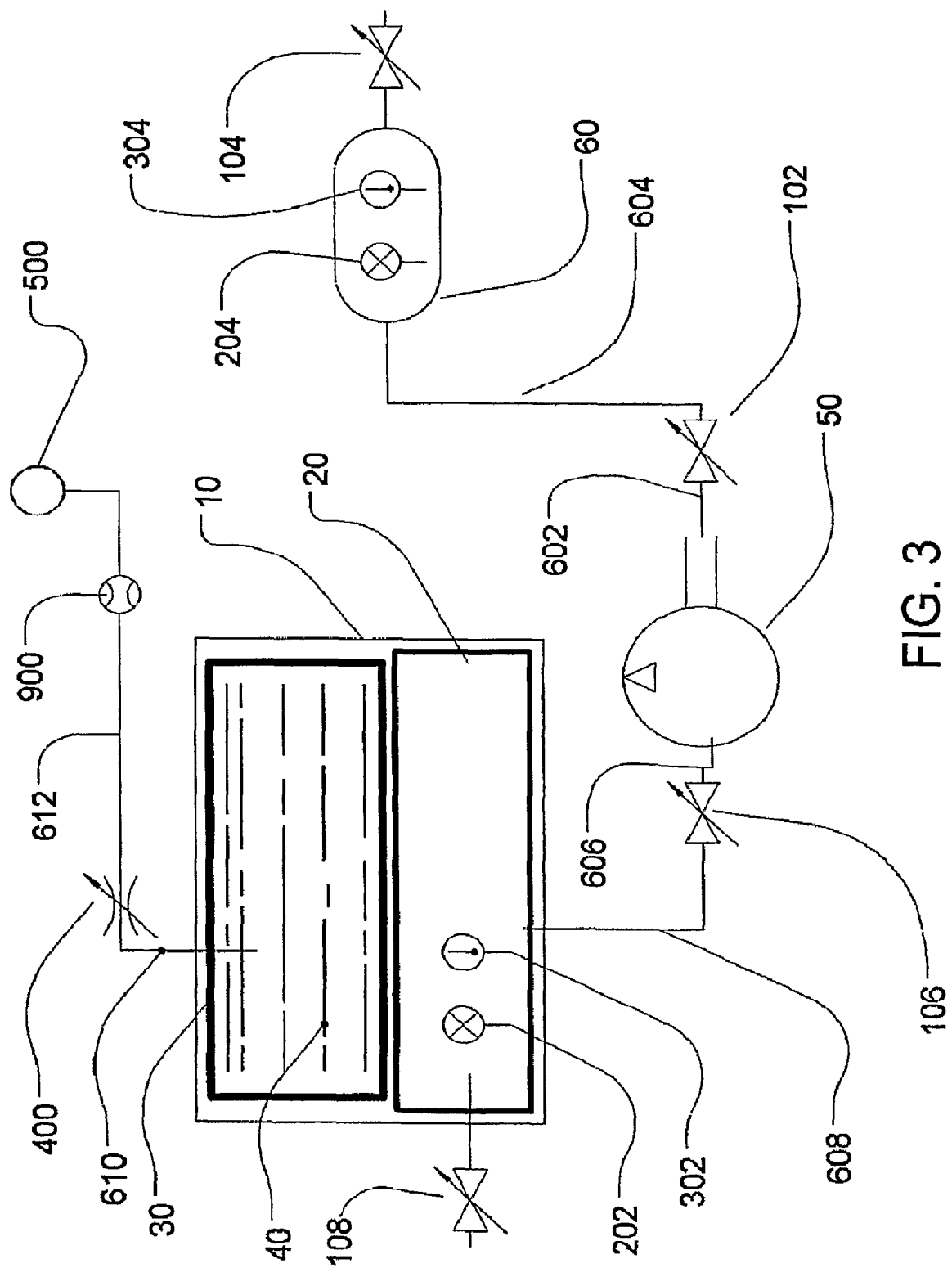
FIG. 3 is a functional block diagram showing the fluidic connections of a volume measurement system according to an exemplary embodiment.

Referring now to FIG. 3, the air bladder 20 is connected to an air pump 50 via a bladder connection line 608, a bladder valve 106, and a bladder valve line 606. The air bladder 20 may be vented to atmosphere via a bladder vent valve 108.

A calibration tank 60 of known volume is connected to the air pump 50 via a tank connection line 604, a tank valve 102, and a tank valve line 602. The tank 60 may be vented to atmosphere via a tank vent valve 104.

The liquid 40 is fluidically coupled to an output 500 via a liquid drain line 610, going through a fluid flow resistor 400 and through an output line 612. The liquid 40 may be, for example, a medication fluid, intravenous solution, or the like, and the output 500 may be, for example, a patient or subject in need thereof. An inline flow sensor 900 is provided in the line 612, as described in greater detail below.

The tank 60 is connected to a tank pressure sensor 204 and a tank temperature sensor 304. The bladder 20 is connected to a bladder pressure sensor 202 and a bladder temperature sensor 302.

Figure 4:
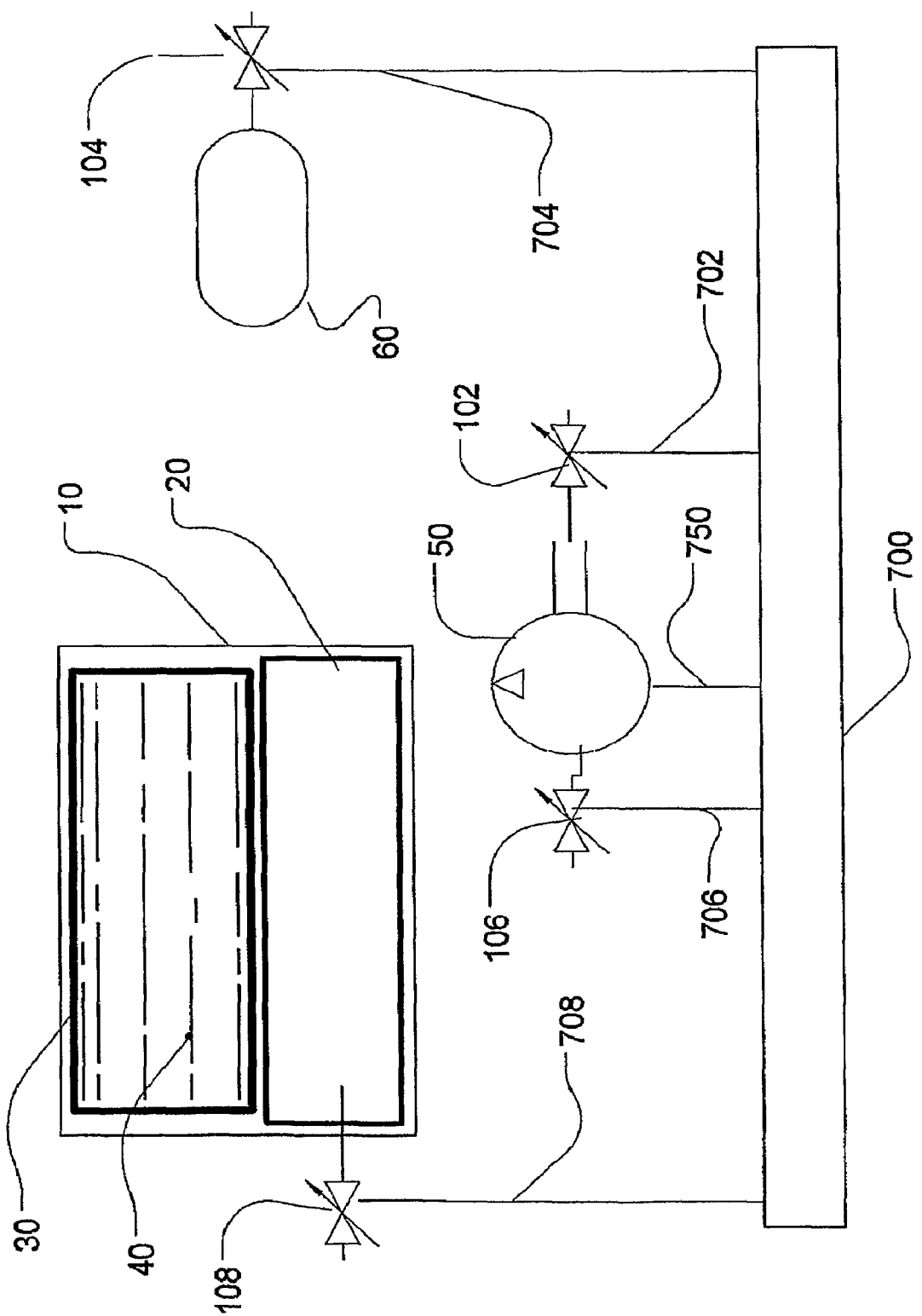
FIG. 4 is a functional block diagram showing the control elements of a volume measurement system according to an exemplary embodiment.

Referring now to FIG. 4, an electronic module includes a processing unit 700 such as a microprocessor, microcontroller, controller, embedded controller, or the like, and is preferably a low cost, high performance processor designed for consumer applications such as MP3 players, cell phones, and so forth. More preferably, the processor 700 is a modern digital signal processor (DSP) chip that offers low cost and high performance. Such processors are advantageous in that they support the use of a 4th generation programming environment that may substantially reduce software development cost. It also provides an ideal environment for verification and validation of design. It will be recognized that the control logic of the present development may be implemented in hardware, software, firmware, or any combination thereof, and that any dedicated or programmable processing unit may be employed. Alternately, the processing unit 700 may be a finite state machine, e.g., which may be realized by a programmable logic device (PLD), field programmable gate array (FPGA), field programmable object array (FPOA), or the like. Well-known internal components for processor 700, such as power supplies, analog-to-digital converters, clock circuitry, etc, are not shown in FIG. 4 for simplicity, and would be understood by persons skilled in the art. Advantageously, the processing module 700 may employ a commercially available embedded controller, such as the BLACK-FIN® family of microprocessors available from Analog Devices, Inc., of Norwood, Mass.

With continued reference to FIG. 4, the processing unit 700 controls the air pump 50 via a pump control line 750. The processor 700 controls the tank vent valve 104 via a tank vent valve control line 704. The processor 700 controls the tank valve 102 via a tank valve control line 702. The processor 700 controls the bladder vent valve 108 via a bladder vent valve control line 708. The processor 700 controls the bladder valve 106 via a bladder valve control line 706.

Figure 5:
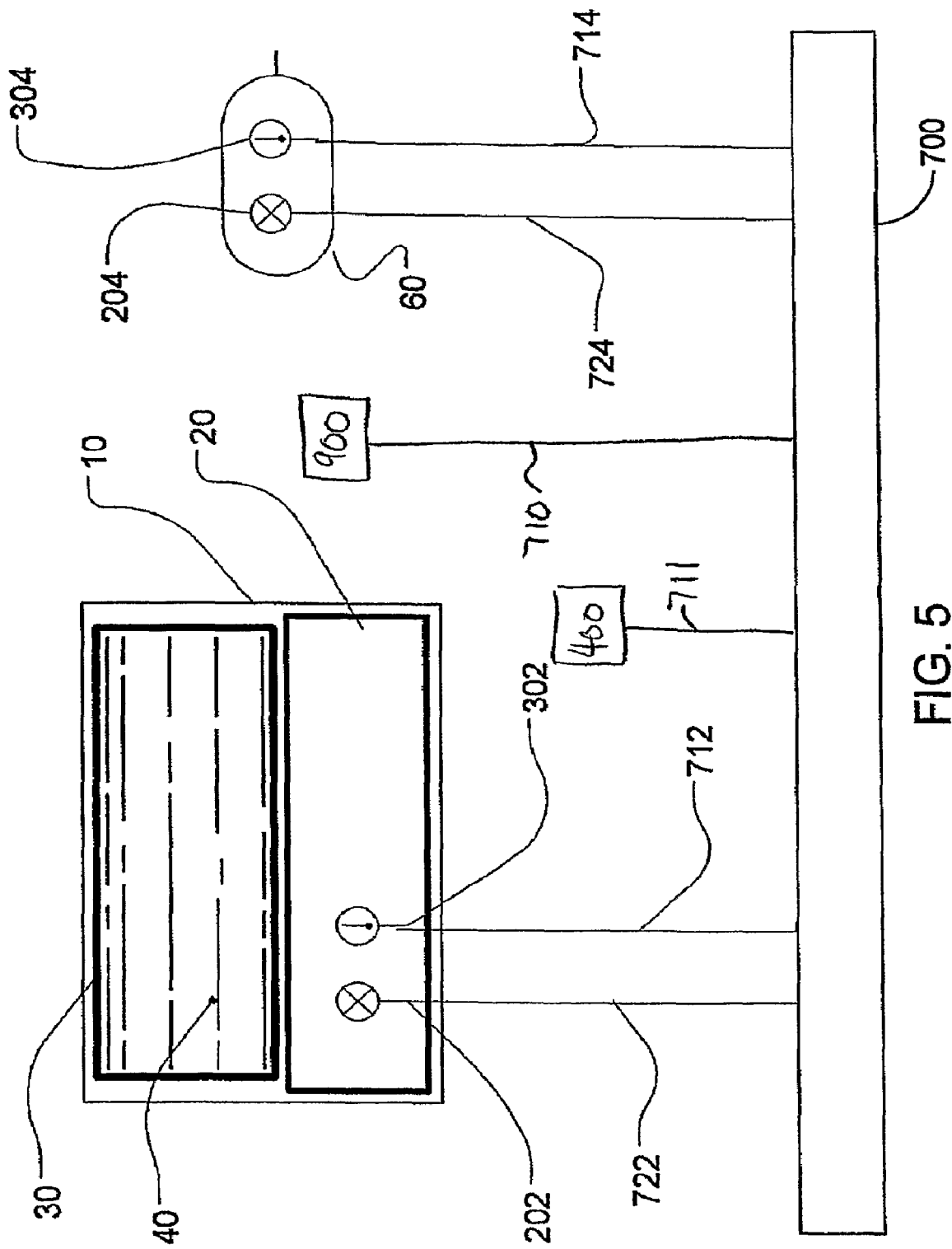
FIG. 5 is a functional block diagram showing the sensing elements of the system.

With reference now to FIG. 5, the processor 700 can measure pressure and temperature from the bladder 20 and tank 60. The processor 700 reads the pressure in the tank 60 via a tank pressure sensor 204, which is coupled to the via tank pressure line 724. The processor 700 reads the pressure in the bladder 20 via a bladder pressure sensor 202, which is coupled to the processor 700 via a tank pressure line 722. The processor 700 reads temperature of the gas in the tank 60 via a tank temperature sensor 304, which is coupled to the processor 700 via a tank temperature line 714. The processor 700 reads the temperature of the gas in the bladder 20 via a bladder temperature sensor 302, which is coupled to the processor 700 via a bladder temperature line 712. The processing system 700 may receive flow rate data from the inline flow sensor 900 via data line 710.

Volume Measurement

Ultimately, the objective of volume measurement is to know the quantity of liquid 40 remaining in an infusion and how that quantity changes over time.

The pressure frame 10 defines a rigid container of known volume, $V_{frame}$. This volume is known by design and is easily verified by displacement methods. Within the pressure frame 10, there is the air bladder 20, which has a nominal capacity greater than the volume $V_{frame}$. When expanded, the bladder must conform to the geometry of the rigid container and its contents. The volume of liquid 40 to be infused, $V_{tbi}$, is equal to $V_{frame}$, less the fixed and known volume of the bladder 20 itself, $V_{blad}$, less any incompressible materials of the bag 30, $V_{bag}$, and less the volume of gas in bladder 20, $V_{gas}$. Once the value $V_{gas}$ is computed, then $V_{tbi}$ may be computed as follows:

$$V_{tbi} = V_{frame} - V_{blad} - V_{bag} - V_{gas}$$

With the following method, at any given point in time, the volume of air contained in the bladder, $V_{gas}$, can be measured and $V_{tbi}$ can be subsequently computed.

For purposes of economy and flexibility, the pump 50 may be an imprecise air pump, such as that of a rolling diaphragm variety, although other types of pumps are also contemplated. The output of such a pump may vary significantly with changes in back pressure, temperature, age of the device, power supply variation, etc. One advantage of the device and method disclosed herein is that they allow an imprecise pump to be used in a precision application, by calibrating the pump in situ.

Figure 6:
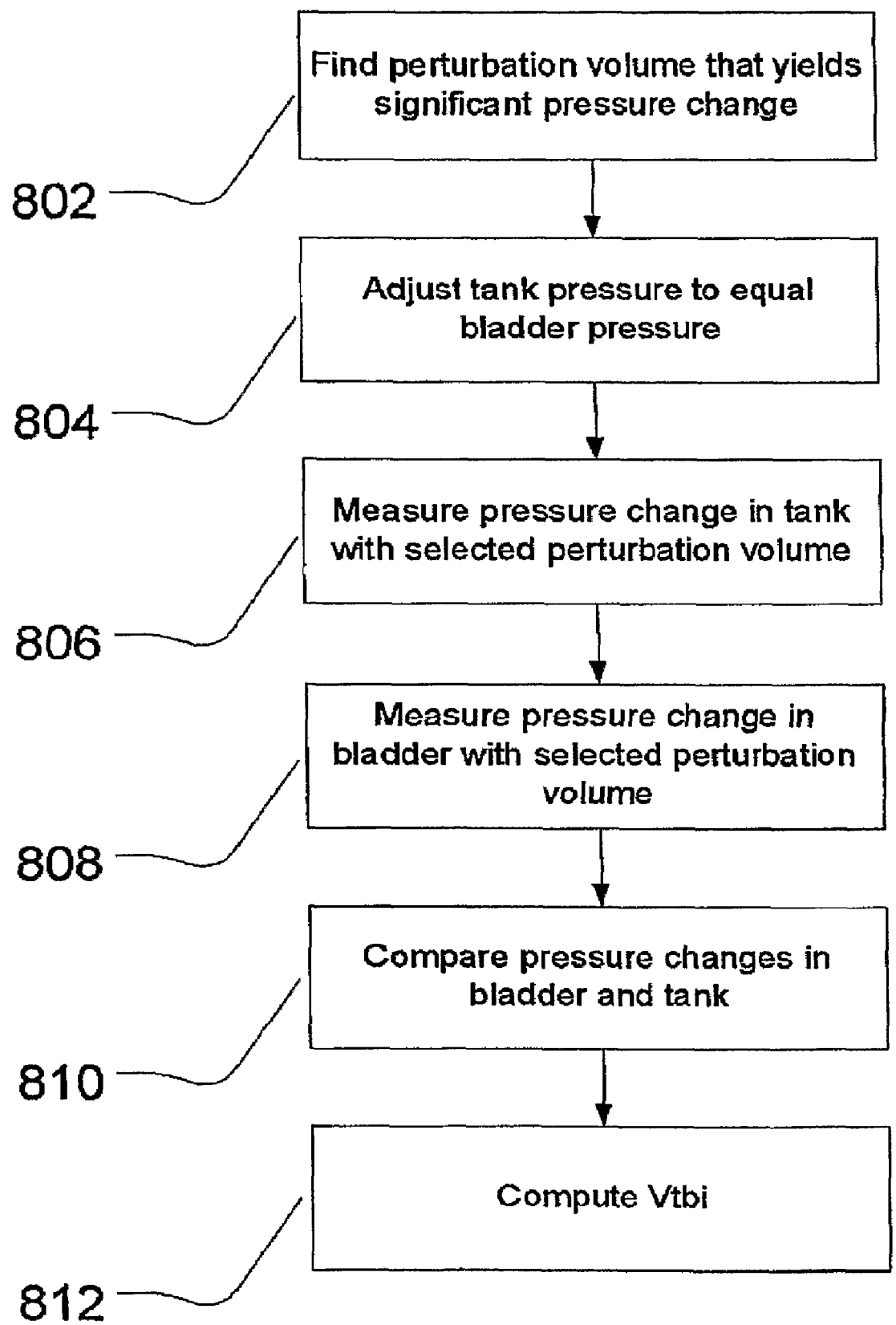
FIG. 6 is a flow chart of an exemplary method for calculating the volume of liquid to be infused.

FIG. 6 shows the steps leading to computation of $V_{tbi}$. Shown as step 802, the first step is to find an optimum amount of air mass, $N_{pump}$, to add to the bladder 20 to effect a significant pressure change, for example, on the order of about 10%. If the amount of air mass added to the bladder is too small, then the pressure change will not be measurable with accuracy. If the amount of the air mass is too great, then pressure in the bladder will increase more than necessary and energy will be wasted.

The initial pressure in the bladder 20, $P_{bladder1}$, is measured using the bladder pressure sensor 202. The tank valve 102 is set to a closed state via the tank control valve line 702 from the processor 700. The bladder valve 106 is set to an open state via the tank control valve line 706 from the processor 700. The pump 50 is activated by the processor 700 via the pump control line 750 for a period of time, $S_{test}$, nominally, for example, about 250 milliseconds. A new measurement of the pressure in the bladder 20 is made, $P_{bladder2}$. Based on the percent of pressure change from this pumping action, a new pump activation time, $S_{pump}$, will be computed. This calculation needs no precision; it is only intended to find an amount of pumping that provides a significant change in pressure, $P_{deltatarget}$, in the bladder 20, for example, on the order of about 10%.

$$S_{pump} = S_{test} * \frac{P_{deltatarget}}{(P_{bladder2} - P_{bladder1})/P_{bladder1}}$$

In step 804, the pump 50 or the tank vent valve 104 are activated to increase or decrease, respectively, the pressure, $P_{tank}$, in the tank 60, so that it approximately equals the pressure, $P_{bladder}$, in the bladder 20. The combination of valve and pump settings required for such adjustments are shown in the table below:

|  | Pump 10 | Bladder Valve 106 | Bladder Vent Valve 108 | Tank Valve 102 | Tank Vent Valve 104 |
|---|---|---|---|---|---|
| Increase $P_{bladder}$ | ON | OPEN | CLOSED | CLOSED | CLOSED |
| Decrease $P_{bladder}$ | OFF | CLOSED | OPEN | CLOSED | CLOSED |
| Increase $P_{tank}$ | ON | CLOSED | CLOSED | OPEN | CLOSED |
| Decrease $P_{tank}$ | OFF | CLOSED | CLOSED | CLOSED | OPEN |

Adjustments made in step 804 can be made iteratively until $P_{tank}$ is roughly equal to $P_{bladder}$, for example, within about 5% of the relative pressure measured in $P_{bladder}$. This does not need to be a precise process. Following the adjustment, the pressure in tank 60, $P_{tank2}$, is recorded.

In step 806, the system is configured to increase the pressure in tank 60, as shown in the above table. The pump 50 is activated for a time period equal to $S_{pump}$. After a delay of approximately five seconds, the pressure in the tank 60 is measured, $P_{tank3}$. This delay is to reduce the effect of an adiabatic response from the increase in pressure in the tank 60.

In step 808, the system is configured to increase the pressure in the bladder 20, as shown in the above table. The pump 50 is activated for a period equal to $S_{pump}$. After a delay of approximately five seconds, the pressure in the bladder 20 is measured, $P_{bladder3}$. This delay is to reduce the effect of an adiabatic response from the increase in pressure in the bladder 20.

Because the initial pressures in the bladder 20 and the tank 60 were approximately equal, the quantity of air mass injected into the tank 60 in step 806 and into the bladder 20 in step 808 will be roughly equal, even though the pump 50 need not be a precise metering device.

We take advantage of several simplifications. First, the ambient temperature for sequential steps 806 and 808 is unchanged. Second, the atmospheric pressure during sequential steps 806 and 808 is unchanged. These conditions simplify the ideal gas law formula and allow the use of gauge pressure measurements, rather than absolute pressure.

In step 810, the volume of gas in the bladder 20, $V_{gas}$, can be calculated with a reduced form of PV=nRT:

$$V_{gas} = \frac{V_{tank} * (P_{tank3} - P_{tank2})}{(P_{bladder3} - P_{bladder2})}$$

As examples of this calculation, if the pressure change were the same in the bladder 20 and the tank 60, then $V_{gas}$ would be equal to $V_{tank}$. If the pressure change in the bladder 20 were 20% as large as that in the tank 60, then $V_{gas}$ would be 5 times greater than $V_{tank}$.

Step 812 derives the value for $V_{tbi}$ from $V_{gas}$, using known values for $V_{frame}$, $V_{blad}$, and $V_{bag}$ and using the calculated value of $V_{gas}$, from step 810.

$$V_{tbi} = V_{frame} - V_{blad} - V_{bag} - V_{gas}$$

The valves 102, 106, 104, and 108 can be configured in many ways, including multiple function valves and or manifolds that toggle between distinct states. The depiction herein is made for functional simplicity, not necessarily economy or energy efficiency.

Flow Rate Measurements

Figure 7:
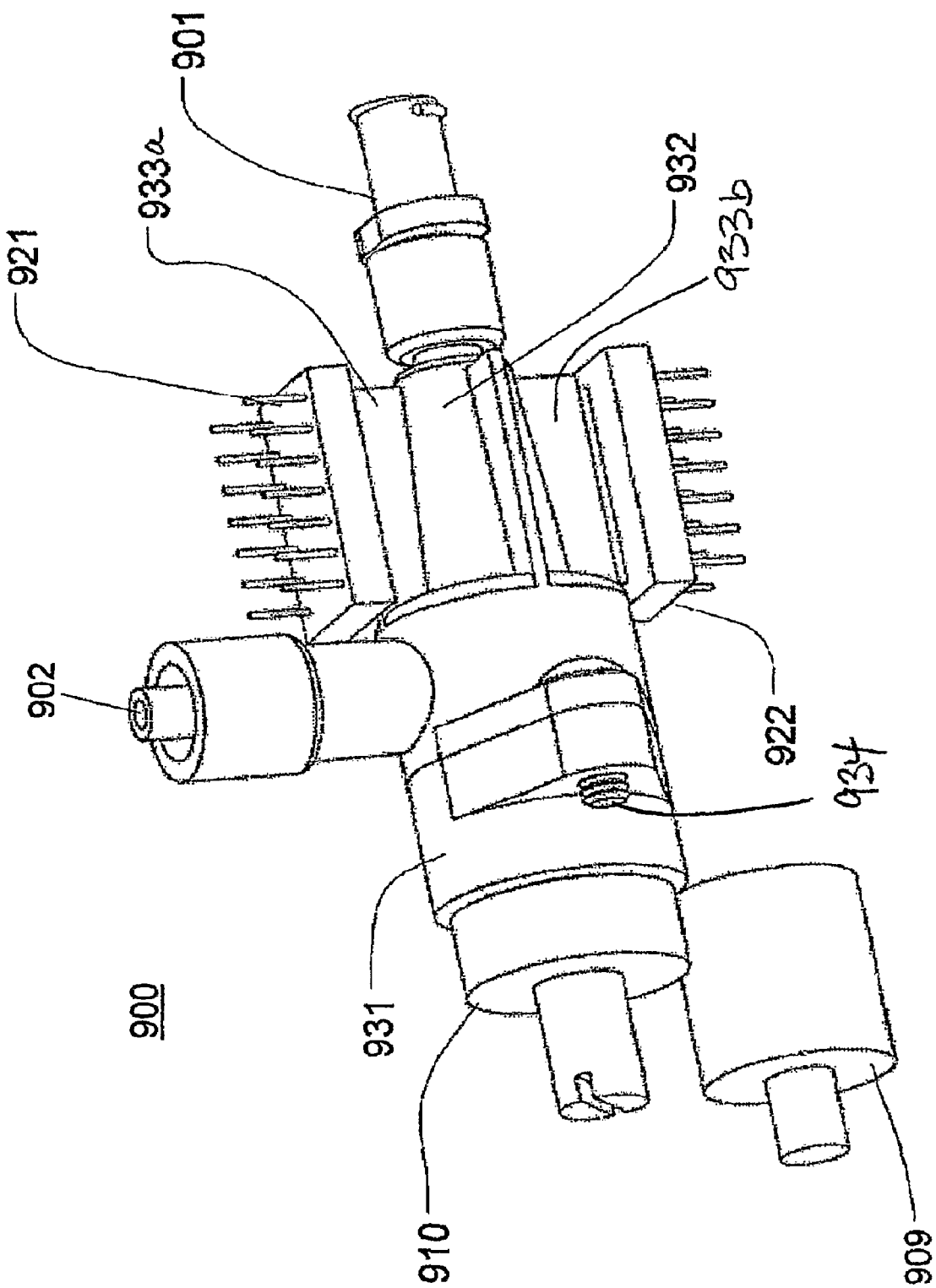
FIG. 7 is a perspective view of the exterior of the flow sensor

FIG. 3 shows the presence of an in-line flow sensor 900 in the output line 612. FIG. 7 shows the external features of an exemplary inline flow sensor 900. Fluid enters an inlet port 901 and exits an outlet port 902, defining a flow path therebetween. An optical sending unit 921 passes light through a proximal housing 932 in general and through optical ribs 933a and 933b. A light pattern is read by an optical sensing array 922. A distal body 931 houses an adjustment mechanism 910 that can be turned by the activation of an adjustment gear 909. The proximal housing 932 and the distal body 931 may be secured via one or more fasteners, such as threaded fasteners 934.

Figure 8:
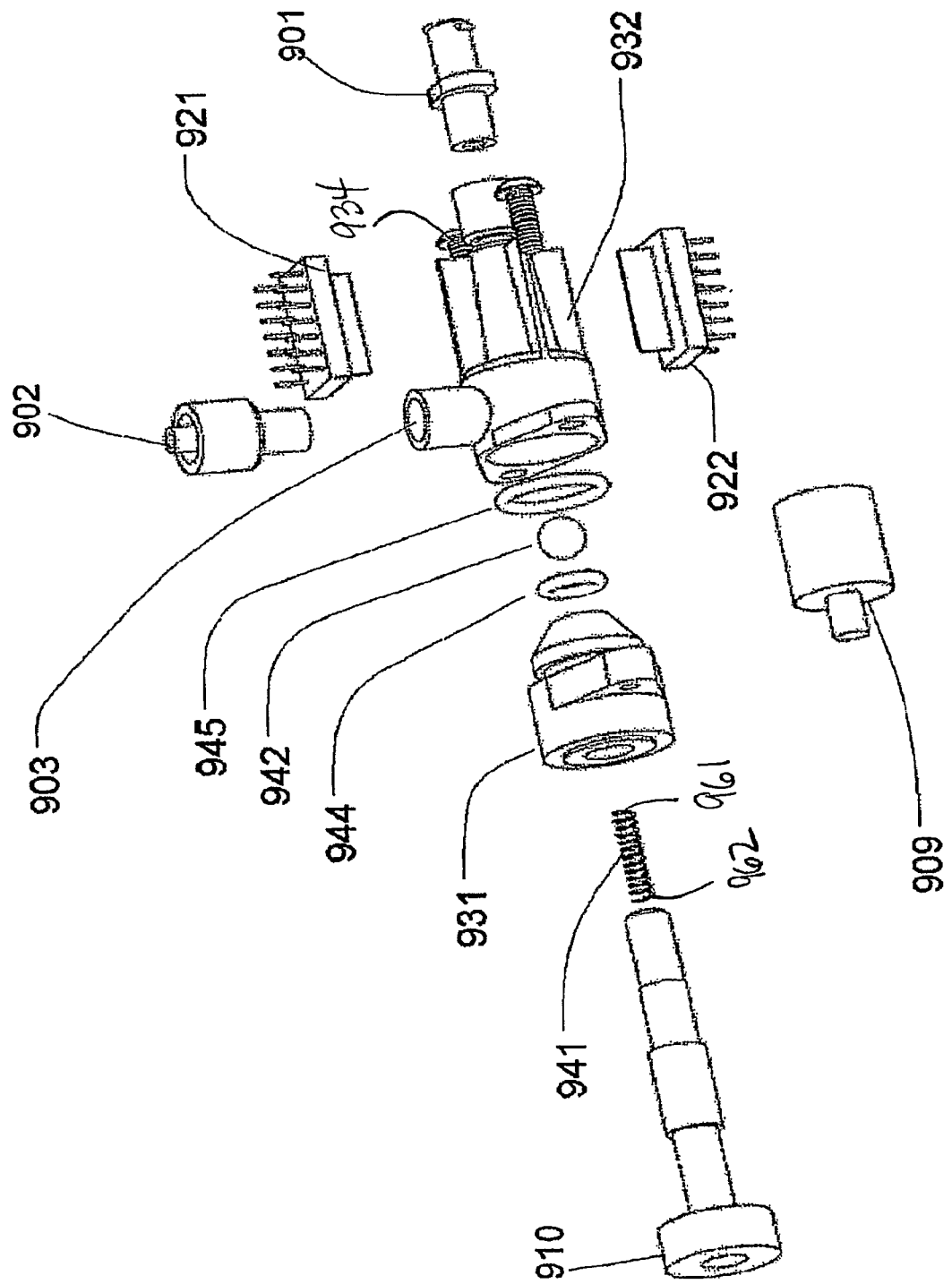
FIG. 8 is an exploded view of the flow sensor.

The exploded view of FIG. 8 shows the internal parts of the inline sensor 900. A first O-ring 945 and a second O-ring 944 are shown in the illustrated preferred embodiment to create a fluid-tight assembly, although other bonding or sealing methods are also contemplated. A compression spring 941, e.g., a cylindrical or conical helical spring includes a first, fixed end 962 received within an axial bore 963 of the adjustment mechanism 910. A second end 961 of the spring 941 bears against a sensor ball 942, which is received within the flow path. The spring 941 applies a force to the sensor ball 942, urging the ball in the direction opposite to the direction of fluid flow. Alternative elements providing this spring function may be, for example, a resilient band, a resilient or compressible material such as a foam structure, and so forth. The adjustment mechanism 910 may be threaded into an axial opening 964 in the distal body 931, e.g., via external helical threads formed on the distal body 931 which are complimentary and mating with internal helical threads within the opening 964. Alternatively, the spring fixed end 962 may be fixed in position and non-adjustable. in such embodiments, the position of the spring fixed end 962 is set by the design in a fixed position of spring pre-load. Rotation of the adjustment mechanism 910 relative to the distal body 931 axially advances or retracts the adjustment mechanism 910, depending on the direction of rotation, and thus causes axial movement of the fixed end 951 of the compression spring 941 to alter the force preload on the sensor ball 942. Alternately, the spring member may be a leaf spring having a first end which is fixed and a second end which is deflectable in the axial or flow direction and which bears against the ball member 942.

Figure 9:
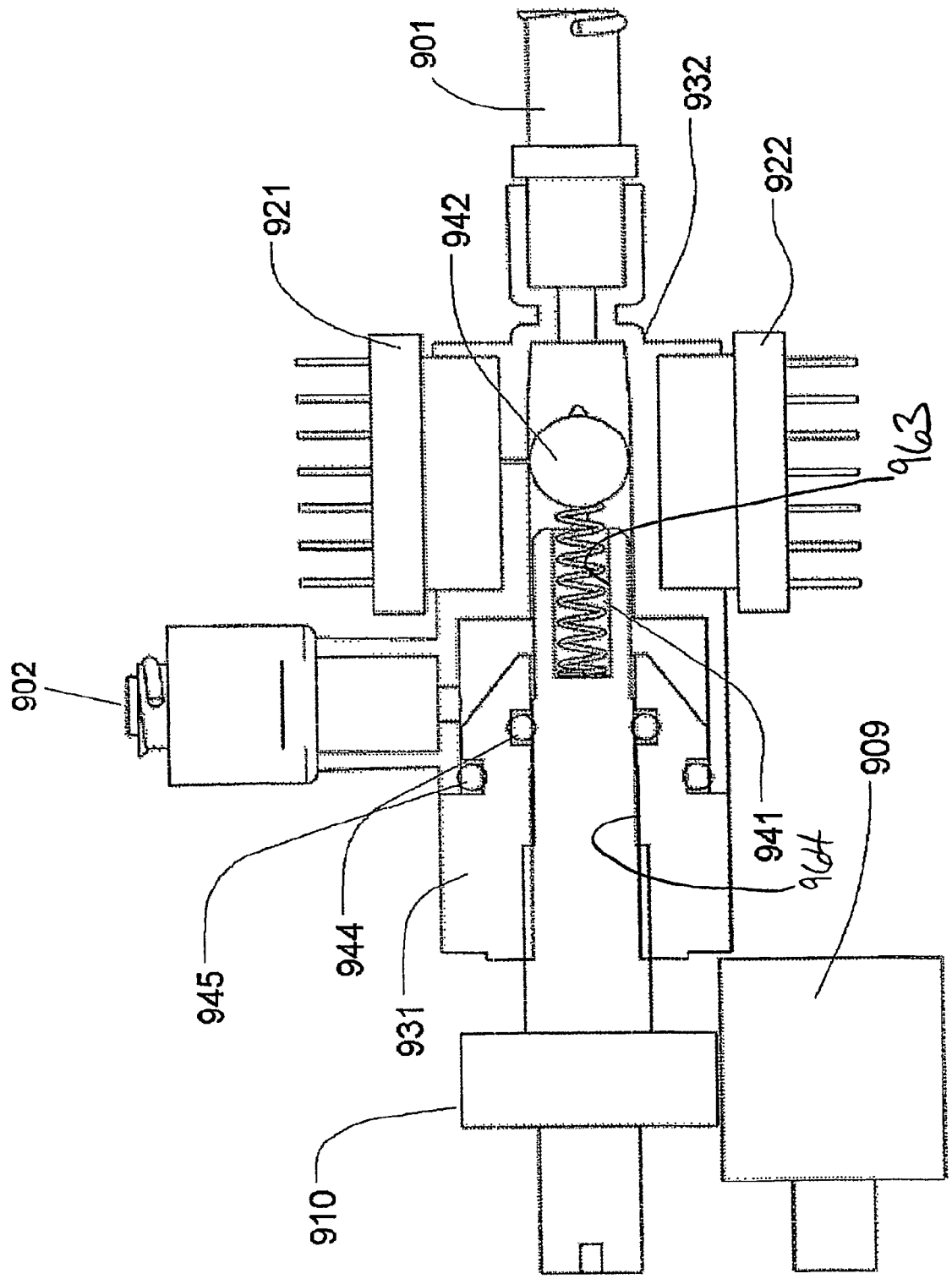
FIG. 9 is a cross-sectional view of the flow sensor
Figure 10:
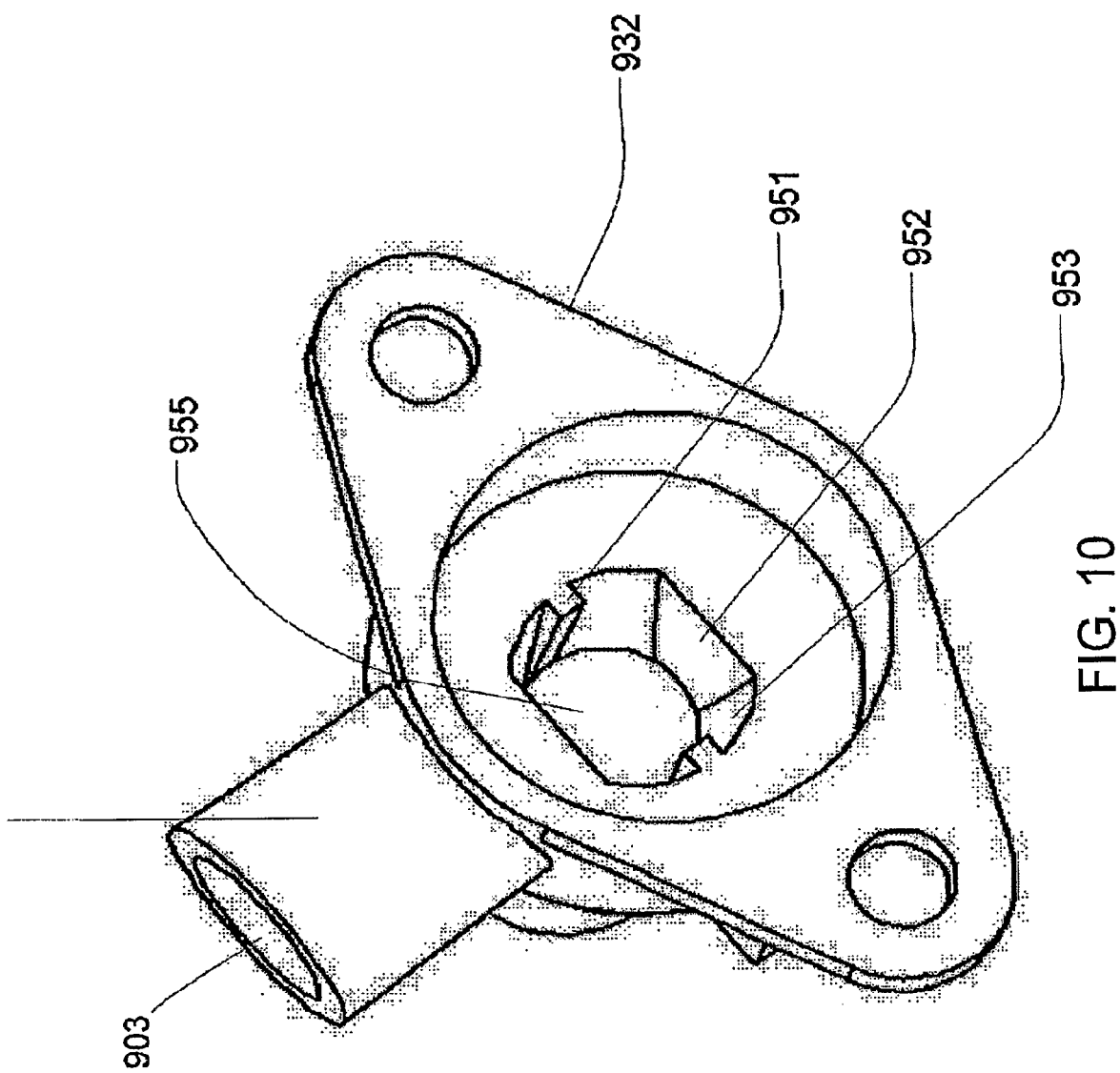
FIG. 10 is a perspective view of the flow sensor housing.

The interior of the proximal housing 932 is shown in FIG. 10. The sensor ball 942 (see, e.g., FIG. 9) axially slides within a cavity 955 defined by the assembly. Optional interior ribs 951 and interior flats 952 may be dimensioned in close tolerance to the sensor ball 942 to allow the sensor ball 942 to travel freely within the cavity 955 while remaining centered in the cavity 955. Tapered walls 953 are fabricated with a draft angle, such that the gap around the sensor ball 942 changes as sensor ball 942 is positioned in different positions within cavity 955.

Referring to the section view of FIG. 9, assume that fluid pressure at inlet port 901 is greater than the fluid pressure at outlet port 902, such that fluid flows from higher pressure to lower pressure. Fluid flow will push on the sensor ball 942 against the urging of the spring 941. Depending on the gap between the sensor ball 942 and the proximal housing 932 and depending on the rate of fluid flow, a force will be exerted upon the sensor ball 942. The compression spring 941 is in contact with the sensor ball 942 such that a spring force is generated to the extent that compression spring 941 is compressed. Fluid traverses beyond sensor ball 942 and exits the assembly via outlet port 902. The gap through which fluid flows between the sensor ball 942 and the proximal housing 932 increases as the sensor ball 942 moves towards compression spring 942.

Figure 11:
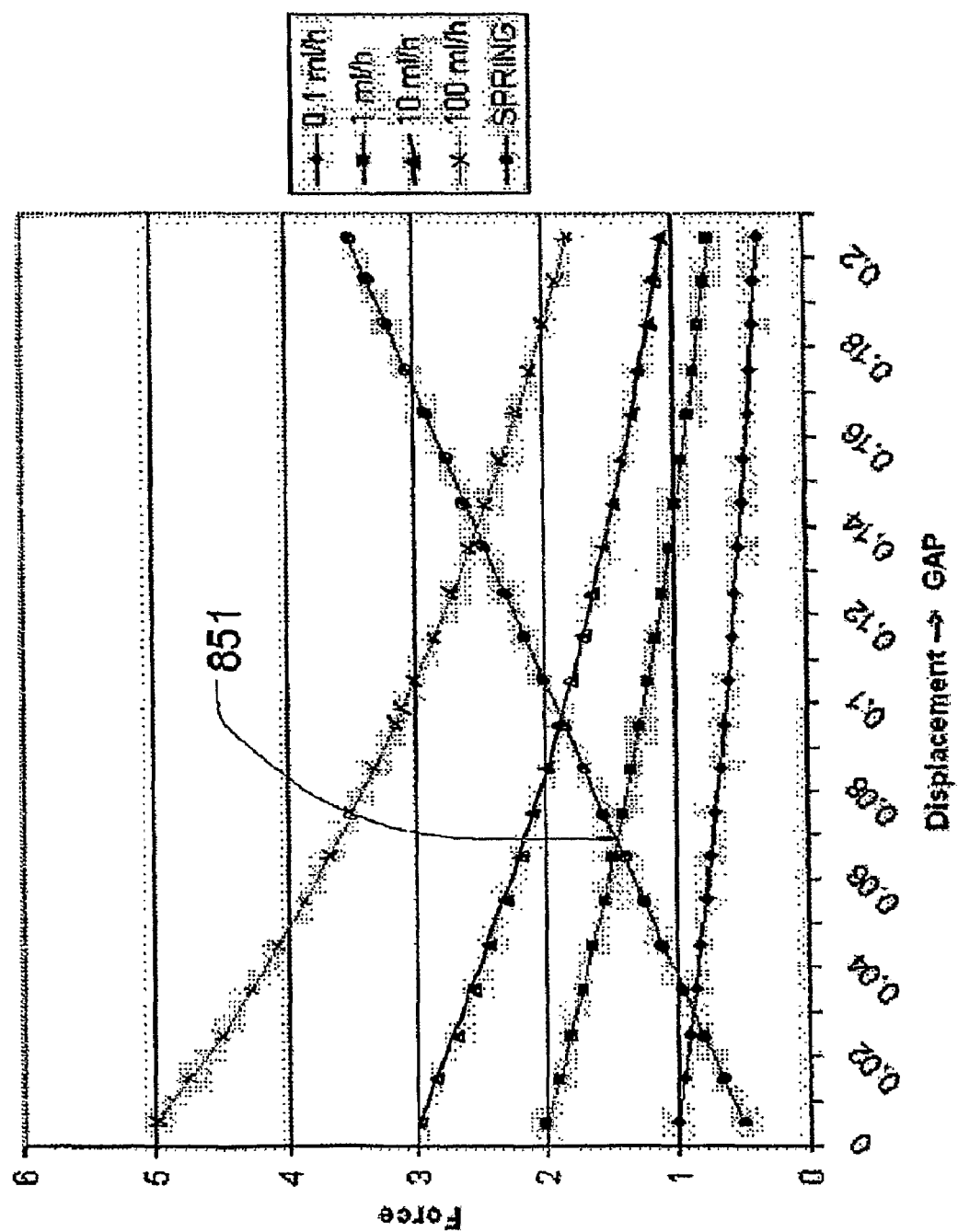
FIG. 11 is a graphical representation of force balancing in the flow sensor.

The graph depicted in FIG. 11 shows the forces created by fluid flow and an opposing spring force. As flow rate increases, the force on the sensor ball 942 will increase, which pushes sensor ball 942 in a manner that has two consequences. First, the gap between sensor ball 942 and proximal housing 932 increases, so that the force applied to sensor ball 942 is reduced due to a larger effective area for fluid to travel around the sensor ball 942. Secondly, the sensor ball 942 moves to increase the force applied by the compression spring 941. The sensor ball 942 thus moves until the force of the compression spring 941 is balanced by the force of the fluid flow against the sensor ball 942. An exemplary equilibrium point 851 is shown in FIG. 11, where the force of the compression spring 941 is balanced with the force created by a flow rate of 1 ml per hour and the sensor ball moves to a displacement approximately 0.07 inches (0.18 cm) away from a seated position of sensor ball 942.

In operation, the light source 921, which may be, for example, an LED array, transmits light through the first optical rib 933a and into the cavity 955. The light incident upon the ball 942 is transmitted through the ball 942 and through the second optical rib 933b to form a light intensity pattern on the photosensor array 922. The photosensor array 922 may be, for example, a charge-coupled device (CCD) array, photodiode array, complimentary metal oxide semiconductor (CMOS) digital detector array, or the like.

The optical transmitter may include one or more light source elements having a wavelength, for example, in the infrared (IR), visible, or ultraviolet (UV) region and the housing and ball member may be formed of a material that optically transmits light of the light source wavelength. The light source may be an array of light elements, such as LEDs, or laser, etc. The light source may be segmented along the axis or may be a continuous, e.g., scanned or otherwise optically formed beam. The light source may illuminate the detector array along its length simultaneously or by sequentially scanning along its length. The refractive effect of a transparent ball member may have a focusing effect on the light passing therethrough that may be detected by the photosensor array. Alternatively, a nontransmissive ball may be employed and the ball position may be determined by detecting the position of a shadow cast by the ball on the photosensor array. In still further embodiment, the ball member may have reflective surface and the optical sensor array may be positioned to detect light reflected from the surface of said ball.

The output of the photosensor array 922 may be passed via the data line 710 to the processing system 700, which may include a position-detection module or circuitry wherein the axial position of the ball 942 within the channel 955 is determined. The axial position of the ball 922 may in turn be used to determine a flow rate and/or calibrate or correlate ball 922 positions with known flow rates calculated by other means such as plural volume measurements made using the method outlined in FIG. 6 over time, or using the pressure decay method outlined in FIG. 12 and described below.

In certain embodiments, the known flow rates corresponding to axial ball positions may be stored in a memory of the processing system 700, for example, in a table, database, or the like. In such embodiments, when an axial position of the ball 922 is measured, the measured position of the ball may be compared with the table of known flow rates and the flow rate corresponding to the measured axial position is then determined. In other embodiments, calibration measurements of axial ball position and known flow rates may be used to derive an algorithmic formula for mapping a measured axial ball position to a corresponding flow rate. In such other embodiments, when an axial position of the ball 922 is measured, the derived algorithmic formula may then be used to determine the flow rate.

While the present disclosure provides a currently preferred implementation of the system herein, it will be recognized that alternate inline flow sensors are also contemplated.

Flow Rate Calculation

Once the fluid volume has been computed, then multiple measurements made over time will yield knowledge of fluid flow rate, which is, by definition, fluid volume changing over time. Repeated measurements of volume over time provided more and more resolution of average flow rate. The average flow rate and the volume of liquid 40 remaining to be infused can be used to estimate the time at which the fluid volume will be delivered. If the infusion is to be completed within some specified period of time, any error between the specified time and the estimated time can be calculated and the flow rate can be adjusted accordingly.

There are situations where the short-term flow rate is of interest. Rather than make repeated volume measurements over a short period of time, there is an alternative approach. Once the gas volume in bladder 20 is known, then the observation of pressure decay in the bladder can be converted directly to a flow rate. It is important to know that the measurement of pressure decay, by itself, is not adequate to compute flow rate. For example, if the pressure were decaying at a rate of 10% per hour, this information cannot be converted into flow rate, unless the starting gas volume is known. As an example, if $V_{gas}$ has been measured to be 500 ml and the absolute pressure is decaying at a rate of 5% per hour, then the flow rate is 5% of 500 ml per hour or 25 ml per hour. The knowledge of the initial volume is critical to compute fluid flow rate.

The measurement of pressure decay is a simple procedure of observing the time the absolute pressure of $P_{bladder}$ to drop by a small, but significant, amount, preferably for example about 2%. Because the processor 700 is capable of measuring times from microseconds to years, this measurement carries a very wide dynamic range. By observing a 2% drop, the change in pressure is well above the noise floor of the pressure measurement system.

Figure 12:
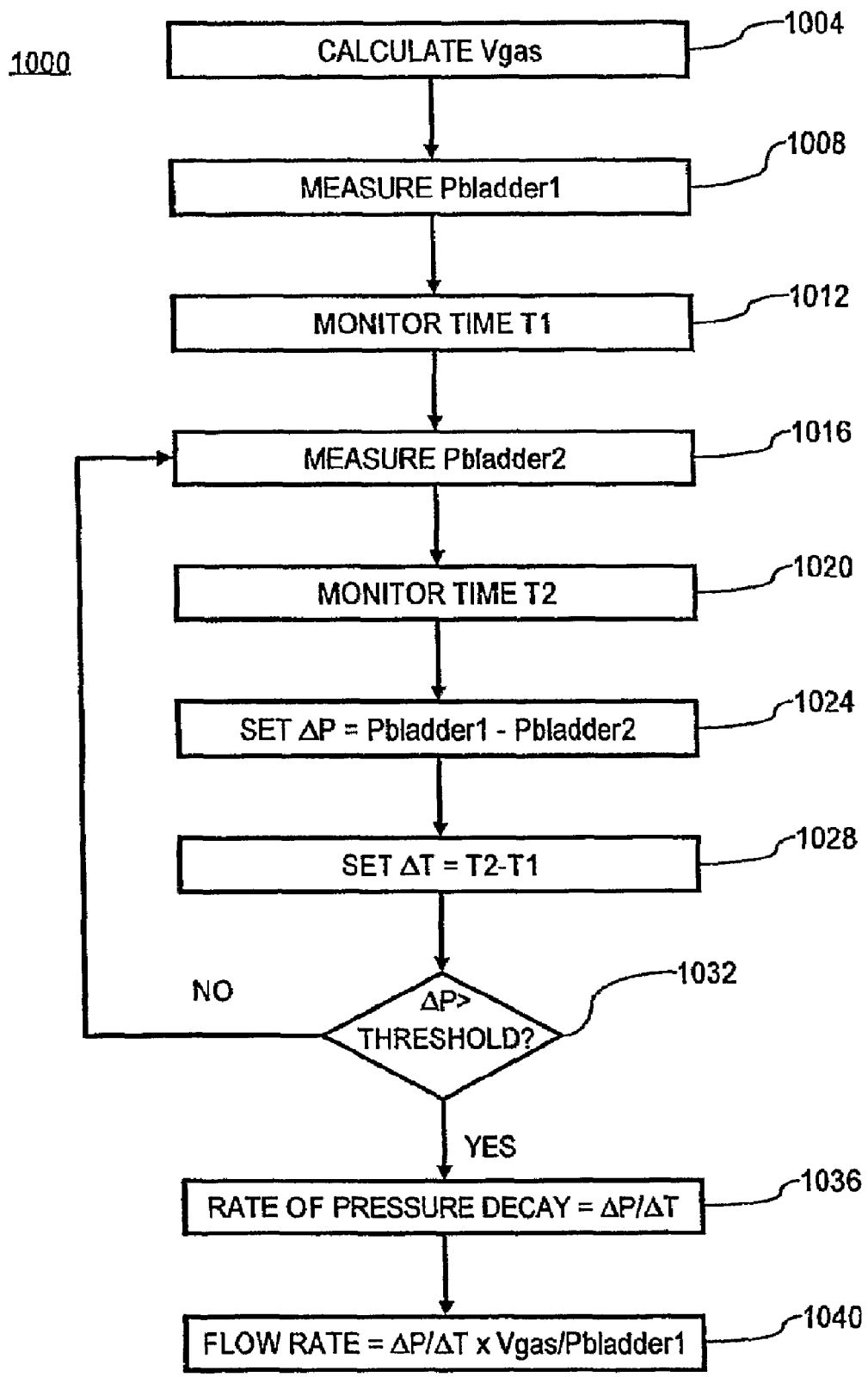
FIG. 12 is a flow chart outlining an exemplary method of calculating flow rate based on pressure decay.

A flow chart outlining an exemplary process 1000 for calculating flow rate by monitoring the rate of pressure decay in the bladder 20 is shown in FIG. 12. At step 1004, the volume of gas in the bladder 20 is calculated as detailed above. At step 1008, the pressure in the bladder 20, $P_{bladder1}$ is measured using the sensor 202 at time T1, which is recorded in step 1012. The pressure in the bladder 20 is measured again at step 1016 and the time T2 is recorded at step 1020. The change in pressure, ΔP, between the time T1 and the time T2 is calculated in step 1024 as $P_{bladder1}-P_{bladder2}$ and the change in time, ΔT, is calculated as T2−T1 at step 1028. At step 1032, it is determined whether ΔP is greater than some predetermined or prespecified threshold value, e.g., about 2% with respect to $P_{bladder1}$. If ΔP has not reached the threshold value at step 1032, the process returns to step 1016 and continues as described above. If ΔP has reached the threshold value at step 1032, the rate of pressure decay is calculated as ΔP/ΔT at step 1036. The flow rate is then calculated as $\Delta P/\Delta T \times V_{gas} - P_{bladder1}$ at step 1040.

Flow Rate Correlations

Figure 13:
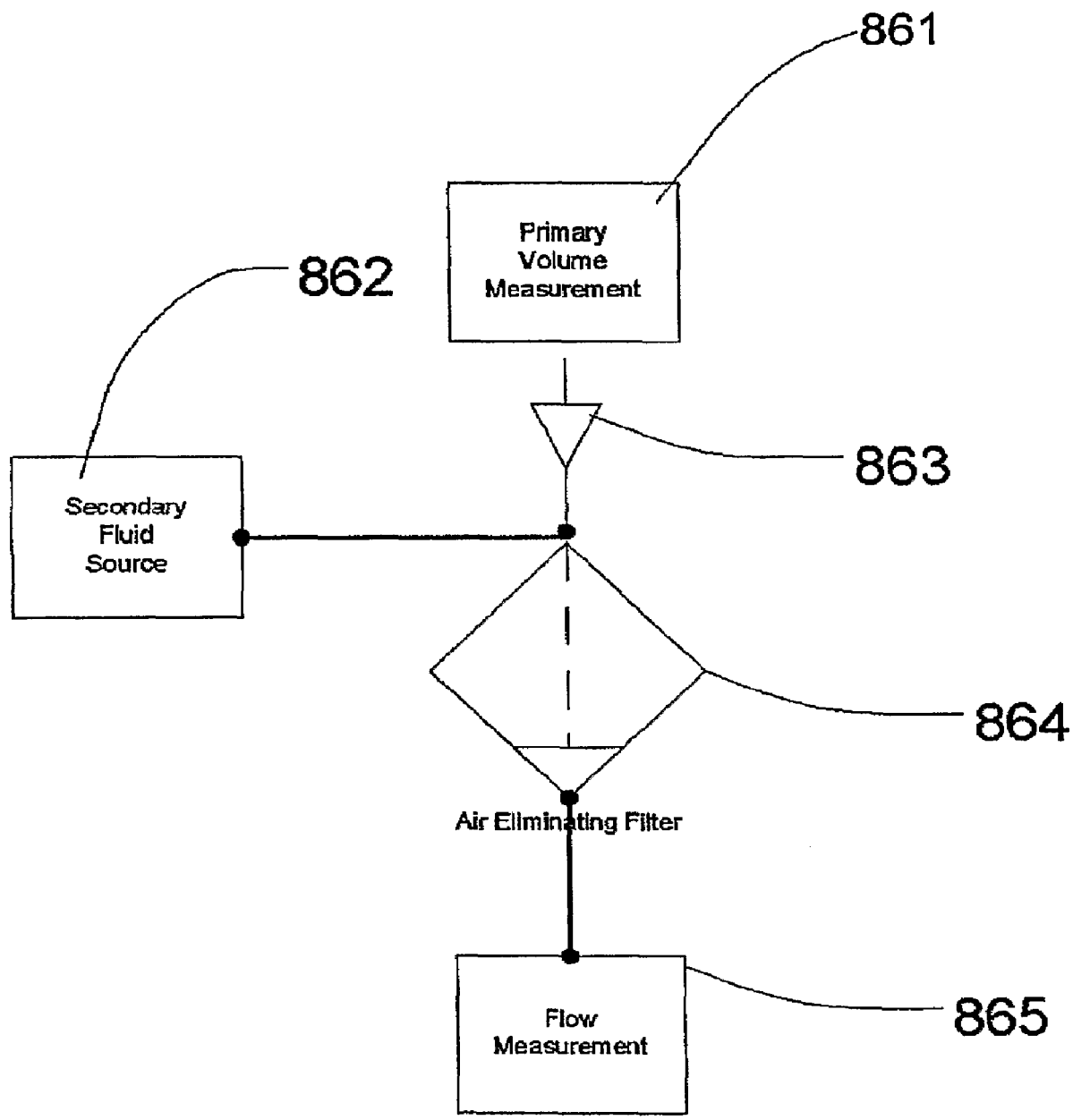
FIG. 13 is a block diagram illustrating an exemplary system having plural, independent methods for measuring flow rate.

The relationship and purpose of having two independent measurement methods for determining flow rate is best described by referring to FIG. 13.

One purpose of the two measurement systems is to calibrate flow measurement 865 with repeated values over time from primary volume measurement 861. Flow measurement 865, e.g., as determined as described above by way of reference to the flow sensor 900, is a measurement of flow rate or the first derivative of fluid quantity with respect to time. If one were to integrate the value of flow measurement 865 over time, the result would be a quantity of fluid. Any errors in this signal would accumulate, providing decreasing volume accuracy over time.

In contrast, an integral signal, such as that from primary volume measurement 861, e.g., calculated using the volume measurement method as described herein, has a fixed error that does not accumulate over time. In fact, as a percentage, the error obtained with an integral signal will decrease over time. As an analogy, if one were to attempt to reach a certain distance in a determined period of time, the use of a speedometer alone would lead to an obvious and significant error. Using this analogy, if one were to use integral measurements, such as those provided by an odometer and a clock, the resultant accuracy would be high.

Flow measurement 865, as described above, operates over a very wide flow rate range and cannot, in any practical way, be calibrated in advance to accommodate manufacturing variances and other environmental factors such as fluid viscosity. For any given fluid flow rate, the signal from flow measurement can be measured and correlated with repeated measurements over time from primary volume measurement 861. For example, if the measurement from flow measurement 865 was observed to a value "x" over a period of ten minutes and a measurement made by primary volume measurement 861 at the beginning of this period was 100 mL and a subsequent measurement made by primary volume measurement 861 at the end of this period was 90 mL, a correlation could be made between flow signal "x" and a flow rate of 10 mL per 10 minutes, or, 60 mL per hour. Flow rate calibration data may be maintained in memory, preferably a nonvolatile memory, of the processing system 700.

Another purpose of the dual measurement system is to distinguish between two sources of fluid directed to the same output. For purposes of distinguishing the source of fluid, assume that flow measurement 865 has been calibrated at various flow rates as described above. If a secondary fluid source 862 is connected to the system, as shown in FIG. 13, and has a fluid driving pressure greater than the fluid within the subsystem for primary volume measurement 861, then the fluid from secondary fluid source 862 will flow towards flow measurement 865 and will block any fluid flow coming from primary volume measurement 861 by the operation of a one way check valve 863. In this case, the signal from primary volume measurement 861 will be unchanging over time. In this circumstance, the non-zero signal from flow measurement 865 will represent fluid flow from the secondary fluid source 862. Alternatively, the flow signal 865 may be integrated to provide an estimate of volume delivered over any period of time. The measurement of volume delivered from secondary fluid source is, in the instance of an intravenous infusion system, an important clinical measurement.

Yet another purpose of the dual measurement system is to detect a condition where gas is expressed from the primary infusion liquid. If a quantity of air leaves the system by way of an in-line air elimination filter 864, then an increased pressure drop will be observed. By itself, this increased pressure drop would indicate that the fluid flow rate increased proportionally. If air were to escape the system from air elimination filter 864, the signal from flow measurement 865 would remain unchanged, providing an indication that the pressure drop should be interpreted as an escape of air, not an increased in fluid flow. In this circumstance, without flow measurement 865, the pressure signal would be interpreted incorrectly.

Yet another purpose of the dual measurement system is to detect a condition where a leak in the pneumatic system exists. If an air leak occurs in the system, a pressure drop will be observed. By itself, this pressure drop would indicate that fluid is flowing from the system. If air were leaking, the signal from flow measurement 865 would be zero, providing an indication that the pressure drop should be interpreted as a leak of air, not as fluid flow. In this circumstance, without flow measurement 865, the pressure signal would be interpreted incorrectly.

Figure 14:
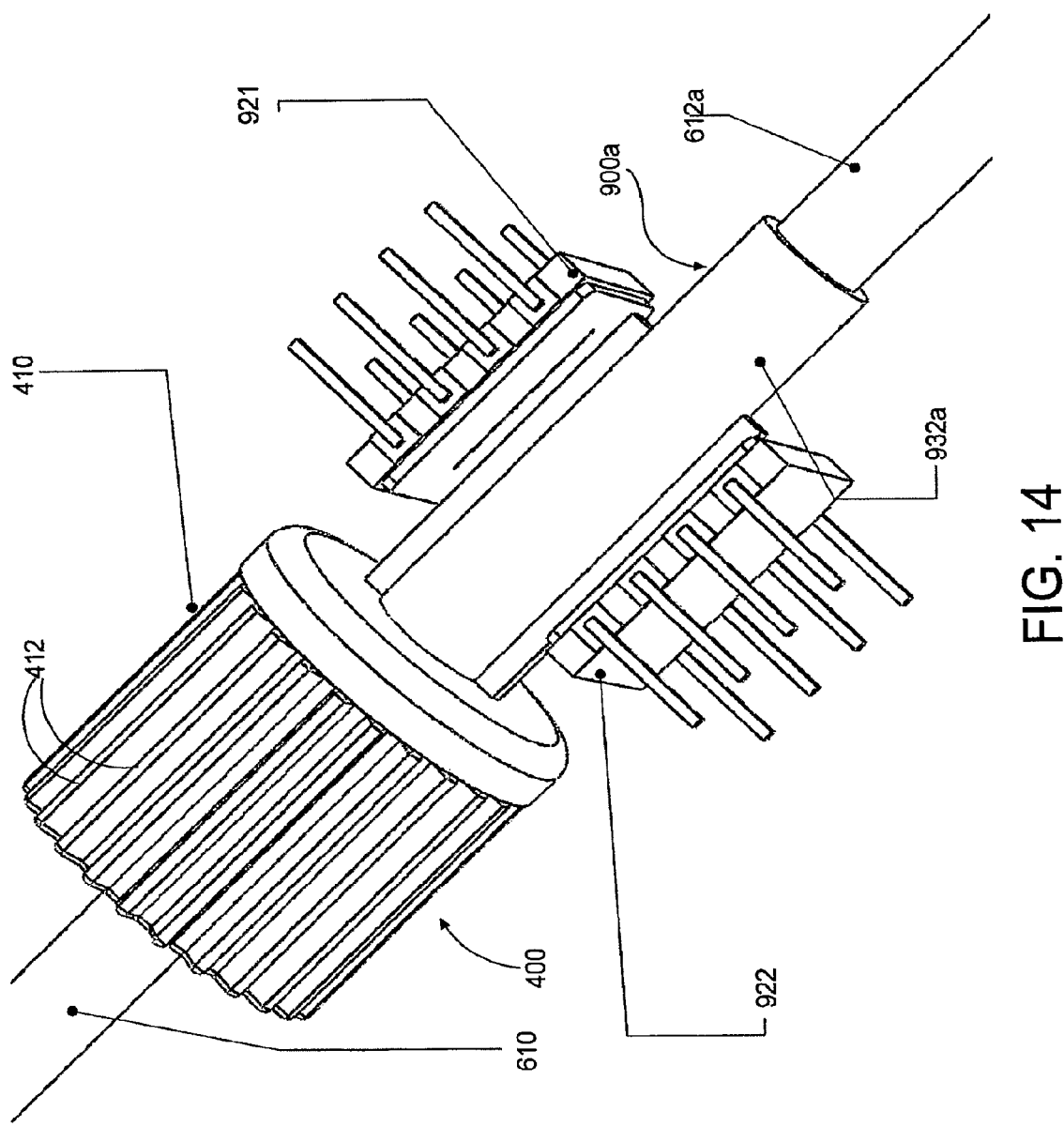
FIG. 14 is an isometric view of an exemplary inline flow resistor and an inline flow sensor.

Referring now to FIG. 14, there is shown an exemplary assembly including an inline fluid flow resistor 400 and an alternative embodiment flow sensor assembly 900*a*. The flow resistor 400 includes an inlet coupled to inlet tube 610 and an outlet fluidically coupled to an inlet of the flow sensor 900*a*. The flow sensor 900*a* includes an outlet fluidically coupled to an outlet tube 612*a*. The flow resistor inlet is fluidically coupled to the fluid source 40, e.g., via fluid line 610. The outlet 612*a* may be fluidically coupled to the vasculature of a patient, e.g., via an IV catheter or cannula (not shown) as are generally known in the art.

The flow resistor 400 includes an exterior housing 410 and includes an adjustment feature for varying the position of a valve in the flow pathway for selectively increasing and decreasing flow resistance.

In the illustrated embodiment, the flow resistor 400 includes a rotatable housing 410, which may have a plurality of radially extending 412 projections forming a gear that may be selectively rotated, e.g., by a stepper motor or other motor having an intermeshing member, or the like. The rotatable housing 410 is coupled to an axially movable needle resistor 414 wherein rotating the housing 410 in one direction causes the needle resistor 414 to move in one axial direction and rotating the housing 410 in the opposite direction causes the needle resistor 414 to move in the opposite axial direction, for example, via helical threads formed on an interior surface of the rotatable housing member 410. It will be recognized that alternative embodiment may include other valve types and/or other adjustment mechanisms, including linearly adjustable linkages between the adjustment mechanism and the valve member.

Figure 15:
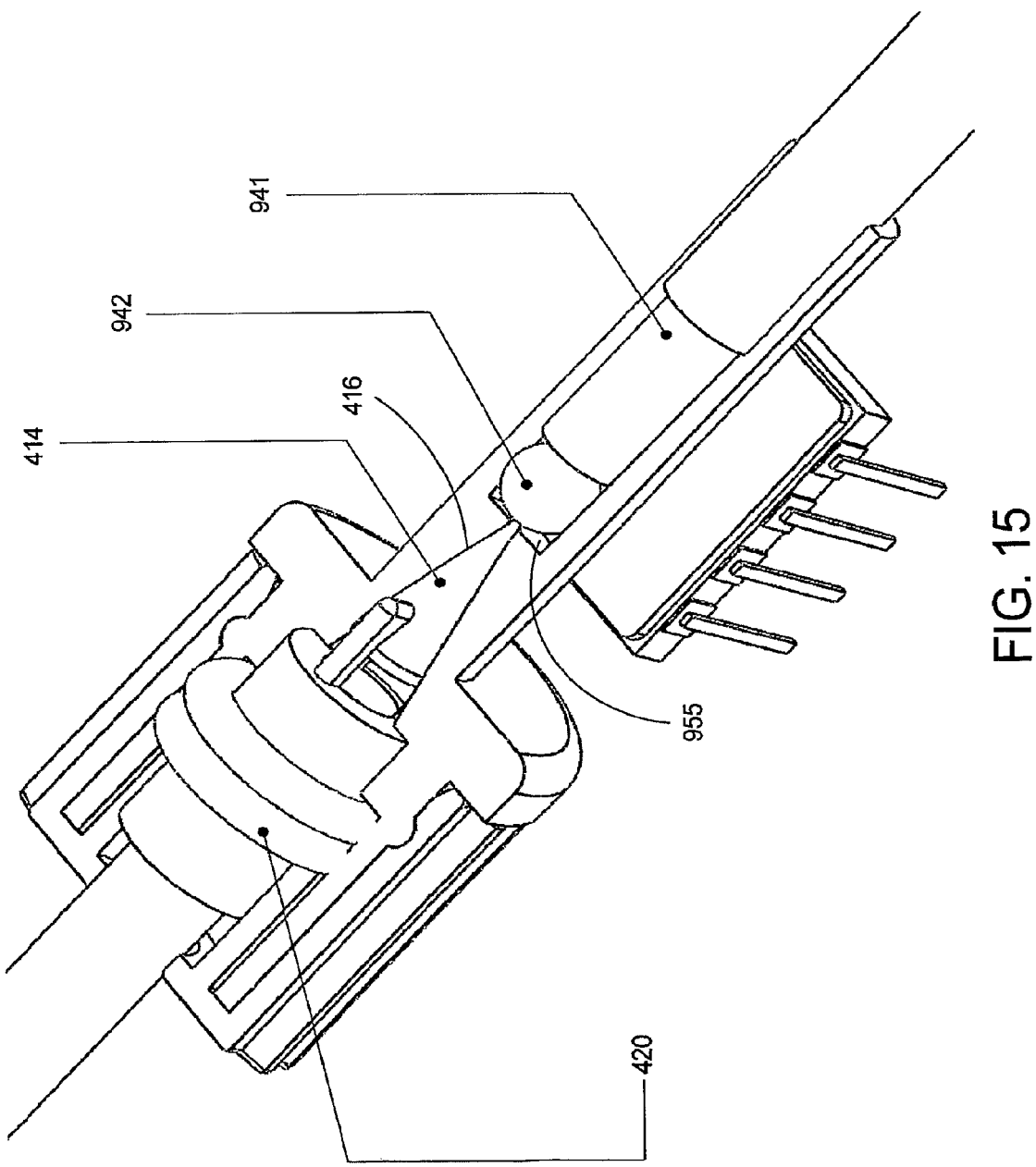
FIGS. 15 and 16 are cutaway views of the inline flow resistor and an inline flow sensor appearing in FIG. 14, with the flow resistor valve in the closed and open positions, respectively.
Figure 16:
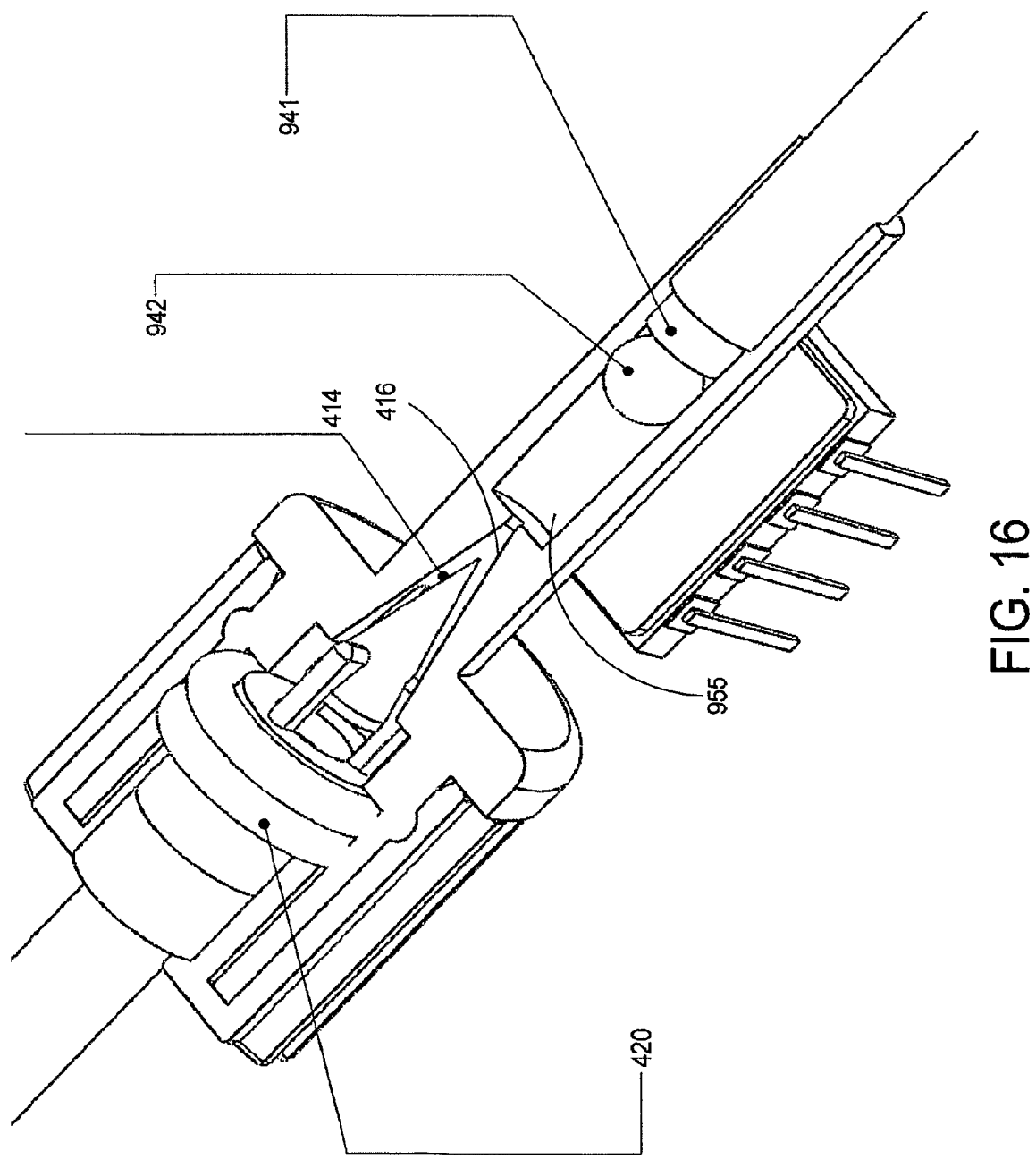
Figure 17:
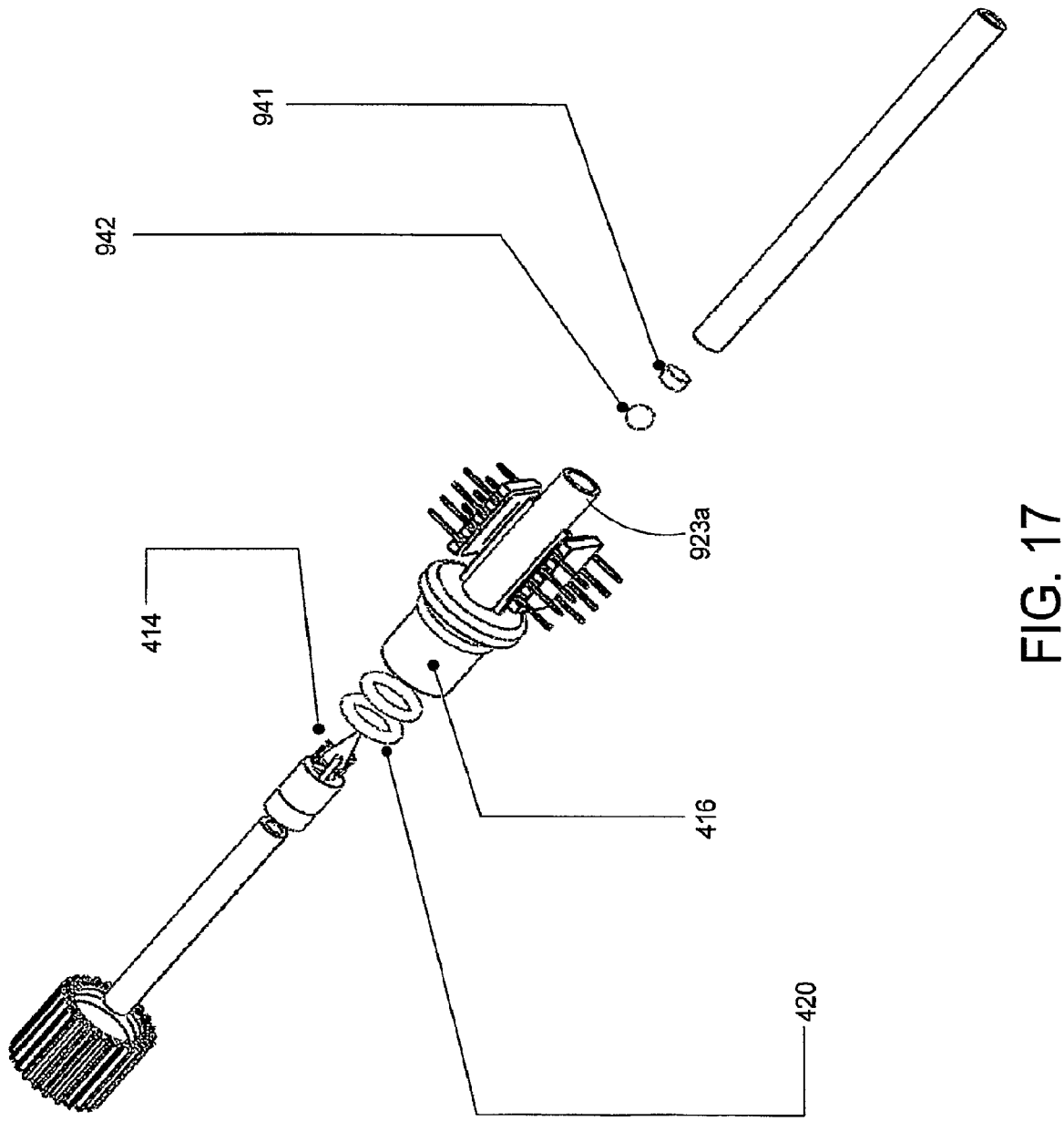
FIG. 17 is an exploded view of the inline flow sensor and flow resistor appearing in FIG. 14.

In the illustrated preferred embodiment, the needle resistor axially moves between a first, closed position (see FIG. 15) wherein the needle resistor engages a mating seat 416 and a fully open position as show in FIG. 16. The annular gap defined between the needle resistor 414 and the seat 416 increases as the valve moves from the closed position to the fully open position, thereby providing a variable flow resistance which varies as a function of the degree of rotation of the housing 410. One or more sealing rings or gaskets 420 may be provided to prevent fluid leakage between the flow passageway and the housing 410.

The flow sensor 900*a* includes a housing member 932*a* defining a cavity 955 receiving a ball member 942. A spring member 941 urges the ball member in a direction opposite to the direction of flow. The spring member 941 may be a resilient compressible material such as a foam member or the like. Alternatively, the spring member 941 may be a coil spring, flat spring, or the like. An optical emitter 921 and an optical sensor 922 sense the position of the ball 942 to determine a flow rate, as detailed above. The inline sensor 400 and flow restrictor 900*a* are depicted as an integral assembly in the embodiment of FIGS. 14-17, however, it will be recognized that the flow resistor and the flow sensor units may be discrete assemblies fluidically coupled in serial fashion.

The present disclosure provides a flow control system that adjusts either or both of the driving pressure in the bladder 20 and the series resistance to flow of the flow resistor 400 such that any flow rate error is minimized. The use of a closed feedback control system is in stark contrast to conventional infusion pumps, which are most often of "open loop" design with additional sensors and switches to alert "out of bounds" conditions.

In operation, a user may enter a target flow rate, e.g., via a user interface of the processing system 700. Alternately, a target flow rate may be calculated based on other input parameters, such as a specified infusion time or time to complete an infusion. Real time flow sensing as described is used to determine the actual flow rate, which is compared to the target flow rate. In the event the actual flow rate differs from the target flow rate, one or both of the bladder driving pressure and the resistance of the flow restrictor 400 may be increased or decreased as necessary until the actual flow rate is equal to the target flow rate or until the difference between the target flow rate and the actual flow rate is less that some preselected threshold.

Figure 18:
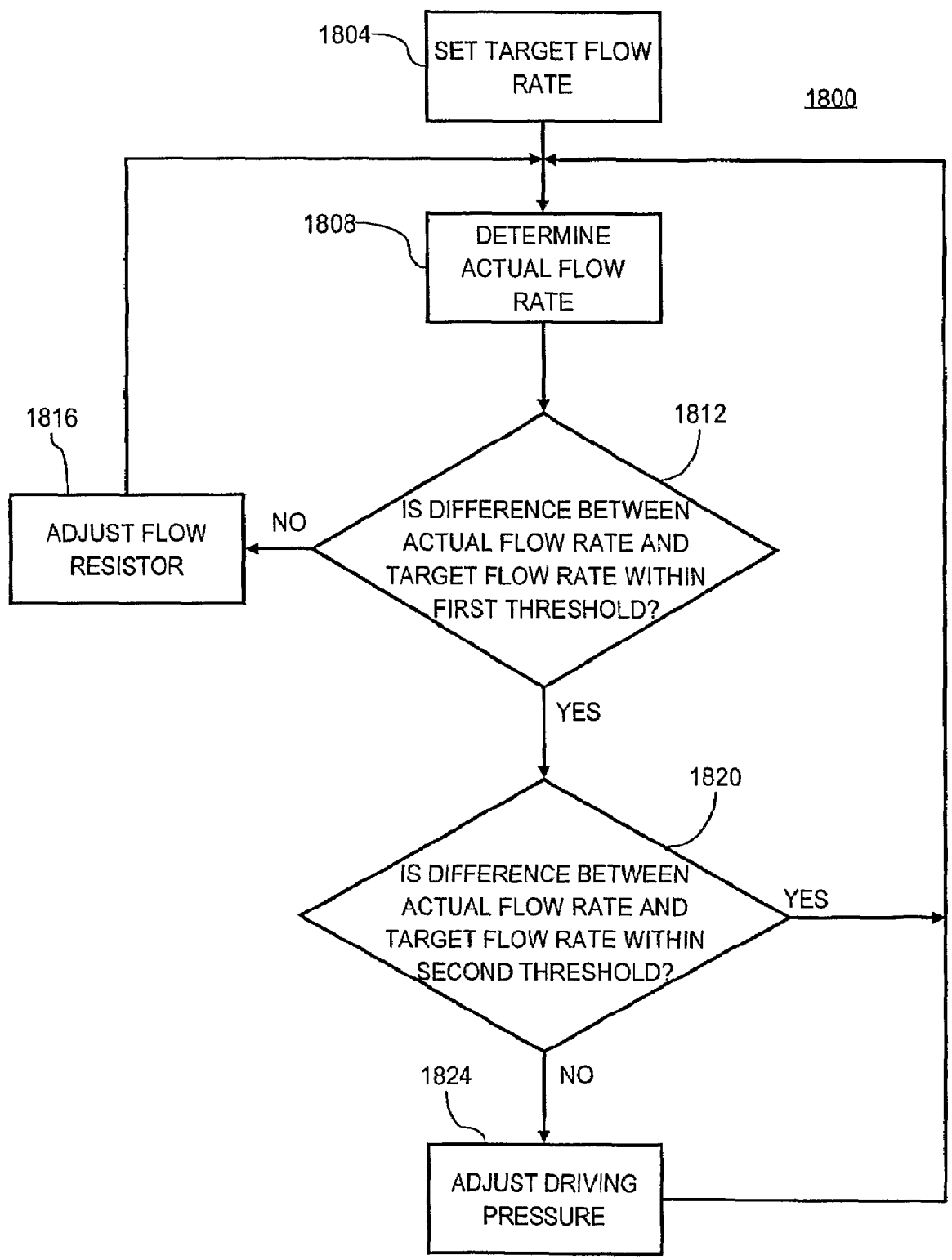
FIG. 18 is a flow chart outlining an exemplary method in accordance with the present disclosure.

Referring now to FIG. 18, there is outlined a preferred exemplary process 1800 for maintaining a desired flow rate. At step 1804, a target or desired flow rate is assigned, e.g., based on user input via a user interface of the processing system 700. At step 1808, the actual flow rate is calculated using one or more of the inline flow sensor 900*a*, calculation of change in the volume of fluid remaining to be infused over time, as detailed above, or monitoring pressure decay as described above.

At step 1812, it is determined whether the difference between the target flow rate and the actual low rate is within a first preselected threshold range. If the actual flow rate is not within this first threshold range, the inline flow resistance is increased or decreased, as necessary depending on the sign of the difference to bring the actual flow rate closed to the target flow rate using the flow resistor 400 at step 1816 and the process returns to step 1808 and repeats. The adjustments may be a series of incremental adjustments to bring the actual flow rate closer to the target flow rate in iterative fashion. In certain embodiments, the control signal for adjusting the inline flow resistor may be proportional to the magnitude of the difference between the actual flow rate and the target flow rate.

If it is determined that the actual flow rate is within the first threshold at step 1812, the process proceeds to step 1820, wherein it is determined whether the difference between the actual flow rate and the target flow rate is within a preselected second threshold range. If the actual flow rate is within the second threshold range at step 1820, the process returns to step 1808 and repeats. If it is determined that the actual flow rate is not within the second threshold at step 1820, the driving pressure in the bladder 20 is adjusted at step 1824 and the process returns to step 1808 and repeats. In this manner, the flow resistor 400 may be used to adjust the actual flow rate until it is relatively close to the target value, and the adjustment of the bladder 20 driving pressure may be used to refine the flow rate to meet the target flow rate precisely. The second threshold value may be selected as a value within which, the actual flow rate is sufficiently close to the target flow rate such that any error in the flow rate is minimal.

In certain embodiments, it may be desirable to maintain a minimum driving pressure in the bladder 20. Thus, the process 1800 may be modified by assigning a minimum pressure threshold value and periodically monitoring the pressure in the bladder. The pressure in the bladder may fall over time, e.g., as a result of fluid leaving the container or as a result of temperature drop. If the pressure falls below the assigned threshold value, the pressure is increased by activation of the pump 50. Preferably, the pump has a stroke volume and compression ratio that puts the new pressure well above the threshold, so no computational hysteresis is required. Each pump cycle may be followed by a new volumetric calculation.

The air pressure threshold value may be selected by a number of factors including the desired flow rate and should be low enough to remain sensitive to patient pressure and resistance, but high enough so as to reduce the level of noise in the in line flow sensor signal. Noise in the flow rate signal may be the result of hydrostatic changes in the system due to patient movement, coughing, transport, or other mechanical disturbances. If the driving pressure in the bladder is too low, the real time flow sensor signal will be noisy, indicating that the flow rate sensor signal is unacceptably affected by patient movement and so forth. However, maintaining a relatively low pressure is desirable in that it reduces energy consumption and remains sensitive to patient pressure and resistance.

In such embodiments employing a minimum pressure threshold, the threshold value may be a fixed value, e.g., representing a compromise pressure that is high enough to reduce noise in the flow rate signal, yet low enough to reduce energy consumption and provide reasonable patient sensitivity. More preferably, however, the assigned pressure threshold value may be dynamically modified over the course of an infusion so as to provide as low a pressure level above the noise threshold as conditions and the selected flow rate permit. In such preferred embodiments, the adjustment of the pressure threshold is made on a continuous or periodic basis using the following criteria. All things being equal, the system will lower the minimum driving pressure threshold periodically, so that the minimal energy is being consumed and the patient is being exposed to the minimal pressure in the line. This is in contrast to the conventional infusion pump designs, where the driving pressures are either highly pulsatile or kept at very high steady levels (e.g., elastomeric pumps). If the real time flow sensor signal is noisy, as can be seen numerically, it indicates that there are hydrostatic changes happening in the system as a result of patient movement, coughing, transport, or other mechanical disturbances. In the presence of this hydrostatic noise, the pressure threshold may be increased to generate a higher operating pressure, which creates immunity from the noise. Then, the pressure threshold is gradually reduced over time, as conditions permit. Furthermore, in such preferred embodiments, if the desired flow rate cannot be met at low pressures, such as with very rapid infusion rates, then the threshold pressure is increased as needed to achieve the desired flow rate.

In certain embodiments, the volume of fluid remaining to be infused may be monitored over an extended period of time for dose rate management. By monitoring the volume of fluid remaining in an infusion over time, the target flow rate can be dynamically adjusted to ensure that an infusion is completed at a prespecified time. That is, periods in which the desired flow rate is not maintained (for example, during a period of occlusion or other slowdown in flow rate, the period when the pressure is being built up in the bladder at the start of an infusion, or after venting the bladder 20 for any reason, etc.) can be offset by a slight increase in the target flow rate so that the infusion is completed on schedule. The time period may be identified via a number of methods. For example, the end time for a given infusion may be input directly via a user interface of the processing system 700. Alternatively, the end time may be calculated based on the calculated volume of infusate and the flow rate input by the operator.

The "titration" of air pressure in the bladder 20 provides an additional, optional form of flow rate control. Even if the flow resistance is kept at a fixed value, the slight adjustment of targeted air pressure refill threshold points may be used to accommodate small adjustments in net flow rates. The signal from the real time in line flow sensor drives this titration process. The titration of air pressure in this manner may be performed separate and distinct from the gross adjustments discussed above. The slight adjustment in pump fill timing is done without any expenditure of energy on the resistor control.

The present disclosure may also measure downstream occlusion. Most infusion devices measure downstream occlusion by an increase in back pressure resulting from a powerful motor, moving fluid in an open loop manner against a resistance. In some cases, the pressure is measured by a limit switch that allows for very significant pressures to be developed distal to the pump. The compliance of the tube can create a hazardous amount of fluid available for bolus into the patient. In contrast, the present device measures fluid flow directly, and thus, an occlusion or slowdown in fluid flow rate can be seen directly. The steady driving pressure and real time flow measurement enhances the visibility of downstream occlusion; whereas, a conventional pump alternates between zero pressure and high pressure so that changes in resistance are not readily visible.

The present disclosure also has the ability to reduce driving pressures. If desired, in face of a potential occlusion, the pressure in the air bladder can be actively reduced to a lower level, for example, via the vent 108. This reduces the chance of an unwanted release bolus.

The present development may also be adapted to detect an upstream occlusion, which creates a particular challenge for many infusion pumps. Some infusion pumps fail to detect the condition all altogether. Since the present system utilizes a pressurized fluid source, the likelihood of an upstream occlusion is reduced. Furthermore, if an upstream occlusion does occur, the multiple flow sensing methods will detect it immediately. Since the present development measures flow rate directly, rather than inferring it, the detection of an upstream occlusion condition can be automatic.

The present development may also be adapted to measure the patient pressure and resistance. In certain embodiments, the present system may use the flow sensor 900 and the ability to reduce the driving pressure in the bladder 20 to periodically determine the exact pressure in the IV line. In such embodiments, the air driving pressure in the bladder 20 can be reduced until such point that the computation of zero crossing for flow rate can be predicted mathematically, thereby eliminating the need to actually reduce the pressure in the bladder to the equilibrium point where flow actually ceases.

In certain embodiments, a direct measurement of the patient resistance can be measured, trended, and used as the basis for an occlusion alarm. Since the driving pressure of the fluid is known from the pressure sensor 202, and the net flow rate is known, then the total resistance to flow is known. The rotational position of the gear housing 410 can also be determined and correlated to a certain fluid flow resistance. If the resistance of the gear 410 is added to the known and fixed resistance of the remainder of fluid pathway and then subtracted from the total resistance, the remainder is the resistance contributed to by the patient.

The invention has been described with reference to the preferred embodiments. Modifications and alterations will occur to others upon a reading and understanding of the

Having thus described the preferred embodiments, the invention is now claimed to be:

1. A fluid delivery apparatus for maintaining a desired flow rate of a fluid from a fluid source along a fluid path, comprising:
    an inflatable bladder bearing against the fluid source to drive the fluid from the fluid source along the fluid path, the flow rate being responsive to varying pressure in said inflatable bladder;
    an adjustable flow resistor for varying flow resistance in the fluid path, the flow rate being responsive to adjustment of said flow resistor;
    an inline flow sensor capable of operating over a wide flow rate range for detecting an actual flow rate of the fluid;
    a processor coupled to said adjustable flow resistor and said flow sensor for comparing the actual flow rate of the fluid with the desired flow rate of the fluid to determine a difference between the actual flow rate and the desired flow rate;
    means for adjusting the flow resistor; and
    means for varying the pressure in said inflatable bladder.

2. The apparatus of claim 1, further comprising:
    said adjustable flow resistor including a valve member in the flow path coupled to an adjustment member, the valve member movable between a first, closed position and a second, fully open position in response to adjustment of said adjustment member.

3. The apparatus of claim 1, further comprising:
    said adjustable flow resistor including a rotatable housing and a valve member in the flow path coupled to the rotatable housing, the valve member movable between a first, closed position and a second, fully open position in response to rotation of said rotatable housing.

4. The apparatus of claim 3, further comprising:
    means for rotating said rotatable housing responsive to the difference between the actual flow rate and the desired flow rate to reduce the difference between the actual flow rate and the desired flow rate.

5. The apparatus of claim 3, wherein said means for rotating said rotatable housing includes a motor controllably coupled to said processor.

6. The apparatus of claim 1, wherein said means for varying the pressure in said inflatable bladder includes a pump fluidically coupled to said bladder for increasing the pressure in the inflatable bladder and a vent valve fluidically coupled to said inflatable bladder for reducing the pressure in said inflatable bladder.

7. The apparatus of claim 6, further comprising:
    means for selectively increasing and decreasing the pressure in said bladder responsive to the difference between the actual flow rate and the desired flow rate to reduce the difference between the actual flow rate and the desired flow rate.

8. The apparatus of claim 1, wherein the fluid is selected from a medication fluid and intravenous solution.

9. A method for maintaining a desired flow rate of a fluid in a fluid delivery device, the fluid flowing from a fluid source along a fluid path, comprising:
    inflating an inflatable bladder that bears against the fluid source to drive the fluid from the fluid source along the fluid path, the flow rate being responsive to varying pressure in said inflatable bladder;
    determining an actual flow rate with an inline flow sensor adapted to sense a real time flow rate over a wide flow rate range and comparing the actual flow rate to the desired flow rate;
    if the actual flow rate is not equal to the desired flow rate, adjusting one or both of pressure in the inflatable bladder and an adjustable flow resistor to reduce the difference between the actual flow rate and the desired flow rate; and
    said adjustable flow resistor for varying flow resistance in the fluid path, the flow rate being responsive to adjustment of said flow resistor.

10. The method of claim 9, further comprising one or both of:
    monitoring a volume of fluid flowing from the fluid source as a function of time; and
    monitoring a rate of pressure decay in said bladder.

11. The method of claim 9, further comprising:
    determining whether the difference between the actual flow rate and the desired flow rate is within a first threshold value;
    if the difference between the actual flow rate and the desired flow rate is not within the first threshold value, adjusting the adjustable flow resistor;
    determining whether the difference between the actual flow rate and the desired flow rate is within a second threshold value; and
    if the difference between the actual flow rate and the desired flow rate is not within the second threshold value, adjusting the driving pressure in the inflatable bladder.

12. The method of claim 11, wherein the second threshold value is less than the first threshold value.

13. The method of claim 9, further comprising:
    calculating a volume of fluid in the fluid source to be infused;
    determining a prespecified time at which at said calculated volume of fluid in the source is to be completed; and
    varying the actual flow rate by adjusting one or both of pressure in the inflatable bladder and the adjustable flow resistor to cause the infusion of the calculated volume of fluid to be completed at said prespecified time.

14. The method of claim 13, wherein said prespecified time is determined by one or more of:
    input of the prespecified time via a user interface of a computer-based information handling system; and
    calculating a completion time based on said calculated volume of fluid and the desired flow rate.

15. The method of claim 9, further comprising:
    said adjustable flow resistor including a rotatable housing and a valve member in the flow path coupled to the rotatable housing, the valve member movable between a first, closed position and a second, fully open position in response to rotation of said rotatable housing.

16. The method of claim 15, further comprising:
    if the actual flow rate is not equal to the desired flow rate, generating a control signal for rotating said rotatable housing proportional to the difference between the actual flow rate and the desired flow rate to reduce the difference between the actual flow rate and the desired flow rate.

17. The method of claim 16, further comprising:
    said adjustable flow resistor is adjusted by rotating said rotatable housing a stepper motor coupled to said processor.

18. The method of claim 9, further comprising:
said inflatable bladder including a pump fluidically coupled to said bladder for increasing the pressure in the inflatable bladder and a vent valve fluidically coupled to said inflatable bladder for reducing the pressure in said inflatable bladder.

19. The method of claim 18, further comprising:
if the actual flow rate is not equal to the desired flow rate, selectively increasing and decreasing the pressure in said bladder responsive to the difference between the actual flow rate and the desired flow rate to reduce the difference between the actual flow rate and the desired flow rate.

20. The method of claim 9, wherein the fluid is selected from a medication fluid and intravenous solution.

* * * * *